(12) United States Patent
Kwak et al.

(10) Patent No.: US 8,541,409 B2
(45) Date of Patent: Sep. 24, 2013

(54) CARBAMOYLOXY ARYLALKANOYL ARYLPIPERAZINE ANALGESICS

(75) Inventors: Byong Sung Kwak, Daejeon (KR); Hong Sik Moon, Daejeon (KR); Han Ju Yi, Daejeon (KR); Young Soon Kang, Daejeon (KR); Dae Joong Im, Daejeon (KR); Eun Hee Chae, Daejeon (KR); Sang Mi Chae, Seoul (KR); Ki Ho Lee, Daejeon (KR)

(73) Assignee: SK Biopharmaceuticals Co., Ltd., Seoul (KR)

( * ) Notice: Subject to any disclaimer, the term of this patent is extended or adjusted under 35 U.S.C. 154(b) by 379 days.

(21) Appl. No.: 12/600,291

(22) PCT Filed: Apr. 30, 2008

(86) PCT No.: PCT/KR2008/002470
§ 371 (c)(1),
(2), (4) Date: Feb. 23, 2011

(87) PCT Pub. No.: WO2008/140198
PCT Pub. Date: Nov. 20, 2008

(65) Prior Publication Data
US 2011/0195963 A1    Aug. 11, 2011

(30) Foreign Application Priority Data

May 14, 2007 (KR) .......................... 10-2007-0046708

(51) Int. Cl.
| | | |
|---|---|---|
| *A61K 31/536* | (2006.01) | |
| *A61K 31/495* | (2006.01) | |
| *A61K 31/496* | (2006.01) | |
| *C07D 265/18* | (2006.01) | |
| *C07D 295/192* | (2006.01) | |
| *C07D 317/60* | (2006.01) | |

(52) U.S. Cl.
USPC .............. 514/230.5; 514/252.11; 514/253.13; 514/254.11; 514/255.03; 544/92; 544/357; 544/360; 544/377; 544/391; 544/379

(58) Field of Classification Search
None
See application file for complete search history.

(56) References Cited

U.S. PATENT DOCUMENTS

| | | | |
|---|---|---|---|
| 3,002,976 A | 10/1961 | Janssen | |
| 3,135,756 A | 6/1964 | Shapiro et al. ................. | 260/268 |
| 4,476,129 A | 10/1984 | Gootjes | |
| 4,605,655 A | 8/1986 | Yevich | |
| 4,988,814 A | 1/1991 | Abou-Gharbia et al. | |
| 5,364,849 A | 11/1994 | Cliffe ............................ | 514/212 |
| 6,838,461 B1 | 1/2005 | Boettcher et al. | |
| 2004/0072839 A1 | 4/2004 | Leonardi et al. ......... | 514/252.12 |
| 2006/0252778 A1 | 11/2006 | Guo et al. | |
| 2007/0208166 A1 | 9/2007 | Baly et al. .................... | 534/766 |
| 2010/0145048 A1 | 6/2010 | Guo et al. | |
| 2012/0095007 A2* | 4/2012 | Lee et al. ...................... | 514/249 |

FOREIGN PATENT DOCUMENTS

| | | |
|---|---|---|
| EP | 0395313 | 12/1999 |
| EP | 1008594 | 6/2000 |
| JP | 61-000075 | 1/1986 |
| WO | WO98/39324 | 9/1998 |
| WO | 02/40466 | 5/2002 |
| WO | 02/48124 | 6/2002 |
| WO | 03068236 | 8/2003 |
| WO | 2004018423 | 3/2004 |
| WO | WO2005/058823 A1 | 6/2005 |
| WO | 2006/112685 | 10/2006 |
| WO | 2006112685 | 10/2006 |
| WO | 2008/019971 | 2/2008 |
| WO | 2008/140197 | 11/2008 |

OTHER PUBLICATIONS

"Pharmaceutical Salts," Journal of Pharmaceutical Sciences, 1977; 66(1): 1-19, Berge et al.
Darmani, N.A., J. Neural Transm., 1998; 105(6-7): 635-643.
The Chilean Office Action mailed Jun. 14, 2012 from the Chilean Patent Office in the corresponding Chilean Patent application No. 2009-2112.
The extended European Search Report by the European Patent Office, issued on Oct. 11, 2010, in the European patent application No. 08753266.9.
The extended European Search Report by the European Patent Office, issued on Oct. 11, 2010, in the European patent application No. 08753270.1.
The International Search Report and Written Opinion by the International Searching Authority, issued on Sep. 26, 2008, in the PCT application No. PCT/KR2008/002466.
The International Search Report and Written Opinion by the International Searching Authority, issued on Oct. 23, 2008, in the PCT application No. PCT/KR2008/002470.
Laduron et al., "In vivo binding of [3H]ketanserin on serotonin S2-receptors in rat brain," European Journal of Pharmacology, vol. 81, Issue 1, Jun. 16, 1982, pp. 43-48.
Middlemiss et al., "Stereoselective blockade at [3H]5-HT binding sites and at the 5-HT autoreceptor by propranolol," European Journal of Pharmacology vol. 101, Issues 3-4, Jun. 1, 1984, pp. 289-293.
Yevich et al., "Synthesis and biological characterization of .alpha.-(4-fluorophenyl)-4-(5-fluoro-2-pyrimidinyl)-1-piperazinebutanol and analogs as potential atypical antipsychotic agents," J. Med. Chem., 1992, 35 (24), pp. 4516-4525.

* cited by examiner

*Primary Examiner* — Emily Bernhardt
(74) *Attorney, Agent, or Firm* — Harness, Dickey & Pierce, P.L.C.; J. Timothy Keane; Kisuk Lee

(57) ABSTRACT

There is provided a novel carbamoyloxy arylalkanoyl arylpiperazine derivative compound having abundant racemic or enantiomeric characteristics, represented by the Formula 1, and pharmaceutically available salts or hydrates thereof. Also, there are provided a pharmaceutical composition for treating pain, anxiety or depression including an effective amount of the compound, and a method for treating pain, anxiety or depression in mammals by administering an effective amount of the compound to the mammals in need of treatment thereof.

19 Claims, No Drawings

CARBAMOYLOXY ARYLALKANOYL ARYLPIPERAZINE ANALGESICS

TECHNICAL FIELD

The present invention relates to novel carbamoyloxy arylalkanoyl arylpiperazine compound, a pharmaceutical compositions comprising the compound and a method for treating pains including acute pain, chronic pain, neurthic pain, post-surgery neuropathic pain, diabetic neuropathic pain, postherpetic neuralgia, inflammatory pain, joint pain, migraine headache and the like, anxiety and depression in mammals by administering the compound to the mammals in need of treatment thereof.

BACKGROUND ART

Up to now, arylpiperazine compounds were proven to be effective to a variety of indications in the field of central nervous system. In particular, U.S. Pat. No. 3,002,976 reported that the following thiophene-engrafted arylpiperazine compound has a pharmacological effect to treat depression. In this formula, R represents hydrogen, methyl group or halogen.

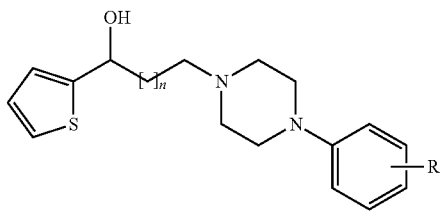

Also, it has been known that effects of buspirone and its structurally related compounds on the treatment of anxiety is due to their selective activities in serotonin (5-hydroxytryptamine: 5HT) sub-type receptor represented by a receptor 5-HT1A. In particular, U.S. Pat. No. 4,988,814 discloses piperazine derivatives showing affinity to the 5-HT1A receptor characterized as therapeutic agents to treat depression and anxiety.

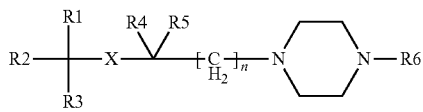

wherein, $R^1$ is alkyl having carbon atoms of 1 to 6; $R^2$ and $R^3$ are each independently alkyl having carbon atoms of 1 to 6, or $R^2$ and $R^3$ are taken together to form polymethylene having carbon atoms of 2 to 12 or to form a 5-norbornen-2-yl residue with carbon atoms bount to the radicals $R^2$ and $R^3$; X is selected from the group consisting of —$CO_2$—, —OCO—, —$OCO_2$—, —N($R^7$)CO—, —NHNHCO—, —ON($R^7$)CO—, —CON($R^7$)—, —N($R^7$)$CO_2$—, —OCON($R^7$)— and —N($R^7$)CON($R^8$) (wherein, $R^7$ and $R^8$ are each independently is selected from the group consisting of hydrogen; alkyl having carbon atoms of 1 to 6; phenyl; benzyl; and phenyl or benzyl substituted by halo, alkyl having carbon atoms of 1 to 6, alkoxy having carbon atoms of 1 to 6, cyano, nitro or perhalomethyl); $R^4$ is hydrogen or alkyl having carbon atoms of 1 to 6; $R^5$ is selected from the group consisting of hydrogen; alkyl having carbon atoms of 1 to 8; hydroxyalkyl having carbon atoms of 1 to 3; phenyl; benzyl; and phenyl or benzyl substituted by hydroxy, halo, alkyl having carbon atoms of 1 to 6, alkoxy having carbon atoms of 1 to 6, trifluoromethyl, nitro, cyano, carbalkoxy having carbon atoms of 2 to 7, carboxamido, amino, alkylamino having carbon atoms of 1 to 6 or dialkylamino having carbon atoms of 2 to 12; $R^6$ is phenyl, benzyl, 2-, 3- or 4-pyridinyl, 2-pyrimidinyl or 2-pyrazinyl that may be substituted by at least one substituents selected from the group consisting of hydroxy, halo, alkyl having carbon atoms of 1 to 6, alkoxy having carbon atoms of 1 to 6, trifluoromethyl, nitro, cyano, carbalkoxy having carbon atoms of 2 to 7, carboxamido, amino, alkylamino having carbon atoms of 1 to 6, and dialkylamino having carbon atoms of 2 to 12; n is one integer selected from the group consisting of 0, 1, 2, 3, 4 and 5, provided that $R^6$ is not 2-pyrimidinyl when X is —CON($R^7$)— (wherein, $R^7$ is alkyl), and $R^6$ is not 3,5-di(trifluoromethyl)phenyl when X is $CO_2$, $R^1$, $R^2$ and $R^3$ are methyl and n is 1.

The present inventors have confirmed that an arylpiperazine structure is correlated with an effect to treat pains as well as anxiety and depression, conducted comprehensive researches on the arylpiperazine structure, and found that novel carbamoyloxy arylalkanoyl arylpiperazine compounds have a medical effect in various pain-induced animal models. In particular, the present inventors have found that the novel carbamoyloxy arylalkanoyl arylpiperazine compounds show their therapeutic effects to treat a wide scope of pains including acute pain, chronic pain, neuropathic pain, post-surgery neuropathic pain, diabetic pain, postherpetic neuralgia, inflammatory pain, joint pain, migraine headache and the like, anxiety and depression. Therefore, the present invention was completed on the basis of the above-mentioned facts.

DISCLOSURE OF INVENTION

Technical Problem

An aspect of the present invention provides a novel carbamoyloxy arylalkanoyl arylpiperazine derivative compound and pharmaceutically available salts or hydrates thereof.

Another aspect of the present invention provides a pharmaceutical composition for treating pain, anxiety or depression including an effective amount of the compound.

Still another aspect of the present invention provides a method for treating pain, anxiety or depression in mammals by administering an effective amount of the compound to the mammals in need of treatment thereof.

Technical Solution

According to an aspect of the present invention, there is provided a novel carbamoyloxy arylalkanoyl arylpiperazine derivative compound having abundant racemic or enantiomeric characteristics, represented by the following Formula 1, and pharmaceutically available salts or hydrates thereof:

Formula 1

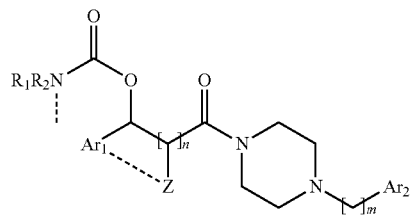

wherein, - - - may selectively form a cyclic ring;

$R_1$ and $R_2$ are each independently selected from the group consisting of hydrogen, straight or branched alkyl having carbon atoms of 1 to 6, and phenethyl, or $R_1$ and $R_2$ may be taken together to form a 5-membered or 6-membered heterocyclic ring or $R_1$ or $R_2$ may be taken together with $Ar_1$ to form a bicyclic ring;

$Ar_1$ is selected from the group consisting of furanyl, thionyl, methylenedioxyphenyl, and phenyl that may be substituted by at least one identical or different substituent selected from the group consisting of hydrogen, straight or branched alkyl having carbon atoms of 1 to 6, halogen such as F, Cl and Br, straight or branched alkoxy having carbon atoms of 1 to 6, nitro, and trifluoromethyl;

Z is hydrogen or fluorine, or may be taken together with $Ar_1$ to form a bicyclic ring;

$Ar_2$ is selected from the group consisting of phenyl, methylenedioxyphenyl, pyridine, pyrimidine, naphthyl, bis(fluoro phenyl)methyl and quinoxaline, all of which may be substituted by at least one identical or different substituent selected from the group consisting of hydrogen, straight or branched alkyl having carbon atoms of 1 to 6, hydroxy, halogen, straight or branched alkoxy having carbon atoms of 1 to 6, nitro, acetyl, t-butylacetyl, trifluoromethyl, amino, and acetate;

n is integer of 1 or 2; and m is integer ranging from 0 to 2.

According to another aspect of the present invention, there is provided a pharmaceutical composition for treating pain, anxiety or depression including an effective amount of the compound having abundant racemic or enantiomeric characteristics.

According to still another aspect of the present invention, there is provided a method for treating pain, anxiety or depression in mammals by administering to the mammals in need of treatment thereof an effective amount of the compound having abundant racemic or enantiomeric characteristics.

Advantageous Effects

As described above, the novel carbamoyloxy arylalkanoyl arylpiperazine derivative compound, and salts and hydrates thereof according to the present invention may be effectively used as a therapeutic agent for treating pains including acute pain, chronic pain, neuropathic pain, post-surgery neuropathic pain, diabetic neuropathic pain, postherpetic neuralgia, inflammatory pain, joint pain and migraine headache and the like, anxiety and depression.

BEST MODE FOR CARRYING OUT THE INVENTION

Hereinafter, the present invention will be described in more detail.

The present invention is related to a carbamoyloxy arylalkanoyl arylpiperazine derivative compound having abundant racemic or enantiomeric characteristics, represented by the following Formula 1, and pharmaceutically available salts or hydrates thereof:

Formula 1

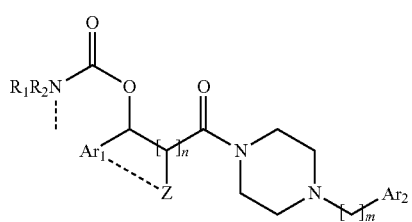

wherein, - - - may selectively form a cyclic ring;

$R_1$ and $R_2$ are each independently selected from the group consisting of hydrogen, straight or branched alkyl having carbon atoms of 1 to 6, and phenethyl, or $R_1$ and $R_2$ may be taken together to form a 5-membered or 6-membered heterocyclic ring or $R_1$ or $R_2$ may be taken together with $Ar_1$ to form a bicyclic ring;

$Ar_1$ is selected from the group consisting of furanyl, thionyl, methylenedioxyphenyl, and phenyl that may be substituted by at least one identical or different substituent selected from the group consisting of hydrogen, straight or branched alkyl having carbon atoms of 1 to 6, halogen such as F, Cl and Br, straight or branched alkoxy having carbon atoms of 1 to 6, nitro, and trifluoromethyl;

Z is hydrogen or fluorine, or may be taken together with $Ar_1$ to form a bicyclic ring;

$Ar_2$ is selected from the group consisting of phenyl, methylenedioxyphenyl, pyridine, pyrimidine, naphthyl, bis(fluoro phenyl)methyl and quinoxaline, all of which may be substituted by at least one identical or different substituent selected from the group consisting of hydrogen, straight or branched alkyl having carbon atoms of 1 to 6, hydroxy, halogen, straight or branched alkoxy having carbon atoms of 1 to 6, nitro, acetyl, t-butylacetyl, trifluoromethyl, amino, and acetate;

n is integer of 1 or 2; and m is integer ranging from 0 to 2.

Also, the present invention is related to a compound represented by the following Formula 2, and pharmaceutically available salts or hydrates thereof:

Formula 2

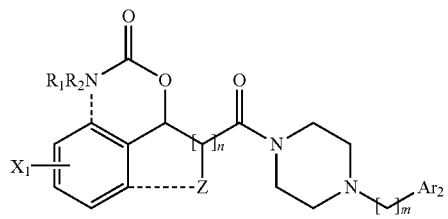

wherein, $R_1$, $R_2$, Z, $Ar_2$, n and m are defined as in the Formula 1; and $X_1$ is at least one selected from the group consisting of hydrogen, straight or branched alkyl having carbon atoms of 1 to 6, halogens such as F, Cl and Br, straight or branched alkoxy having carbon atoms of 1 to 6, nitro, and trifluoromethyl, provided that, when $X_1$ is at least two selected from the groups, the two substituents may be identical to, or different from each other.

In addition, the present invention is related to a compound represented by the following Formula 3, and pharmaceutically available salts or hydrates thereof:

Formula 3

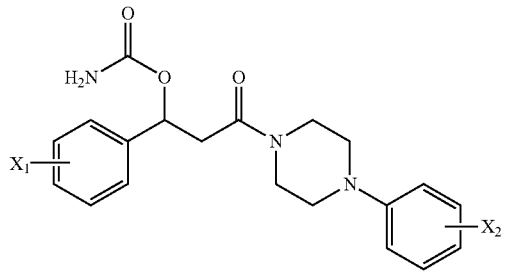

wherein, $X_1$, $R_1$, $R_2$, $Z$, $Ar_2$, n and m are defined as above; and $X_2$ is at least one selected from the group consisting of hydrogen, straight or branched alkyl having carbon atoms of 1 to 6, hydroxy, halogen, straight or branched alkoxy having carbon atoms of 1 to 6, nitro, acetyl, t-butylacetyl, trifluoromethyl, amino, acetate, and acetate, provided that, when $X_2$ is at least two selected from the groups, the two substituents may be identical to, or different from each other.

The compounds according to one exemplary embodiment of the present invention may be chemically synthesized as in the following Schemes 1 and 2. However, they are described for the purpose of illustrations only, and the present invention is not particularly limited thereto.

In the following Schemes, HX represents acids that may form pharmaceutically available salts with a compound having basic nitrogen atoms. The acids includes, for example, hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzenesulfonic acid, methanesulfonic acid, ethanesulfonic acid, hydroxymethanesulfonic acid and hydroxyethanesulfonic acid, but the present invention is not particularly limited thereto. Additional acids may refer to a literature ["Pharmaceutical Salts," *J. Pharm. Sci.*, 1977; 66(1): 1-19]. The preparation of the compound of the present invention is carried out in a reaction medium that may be illustrated as an ether solvent (tetrahydrofuran, ethylether, propylether, isopropylether, and butylether), an alcohol solvent(methanol, ethanol, and isopropyl alcohol), an ester solvent (ethyl acetate), a halogenated hydrocarbon solvent (dichloromethane, chloroform) and mixtures thereof.

Acetophenone substituted by $X_1$ as shown in the Scheme 1 and a compound (1-2) are refluxed in a toluene solvent to synthesize a compound (1-3). The compound (1-3) is reduced with sodium borohydride ($NaBH_4$) to obtain an alcohol intermediate (1-4), and the alcohol intermediate (1-4) is reacted with 1,1-carbonyldiimidazole (CDI), and then with various amines ($NHR_1R_2$) to obtain a compound (1-5). In the Scheme 1, HX represents acid that may produce pharmaceutically available salts with basic amine. According to the Scheme 1, the compound (1-5) is dissolved in a reaction medium such as an ether solvent (tetrahydrofuran, ethylether), an ester solvent (ethyl acetate), a halogenated hydrocarbon solvent (dichloromethane, chloroform), or the like, and corresponding HX is added slowly to obtain a salt compound (1-6). In particular, hydrochloric acid and methanesulfonate salt are generally prepared, and their medicinal effects are measured. Also, the reaction product (1-5) or (1-6) prepared in the Scheme 1 is obtained all in the form of racemic compound.

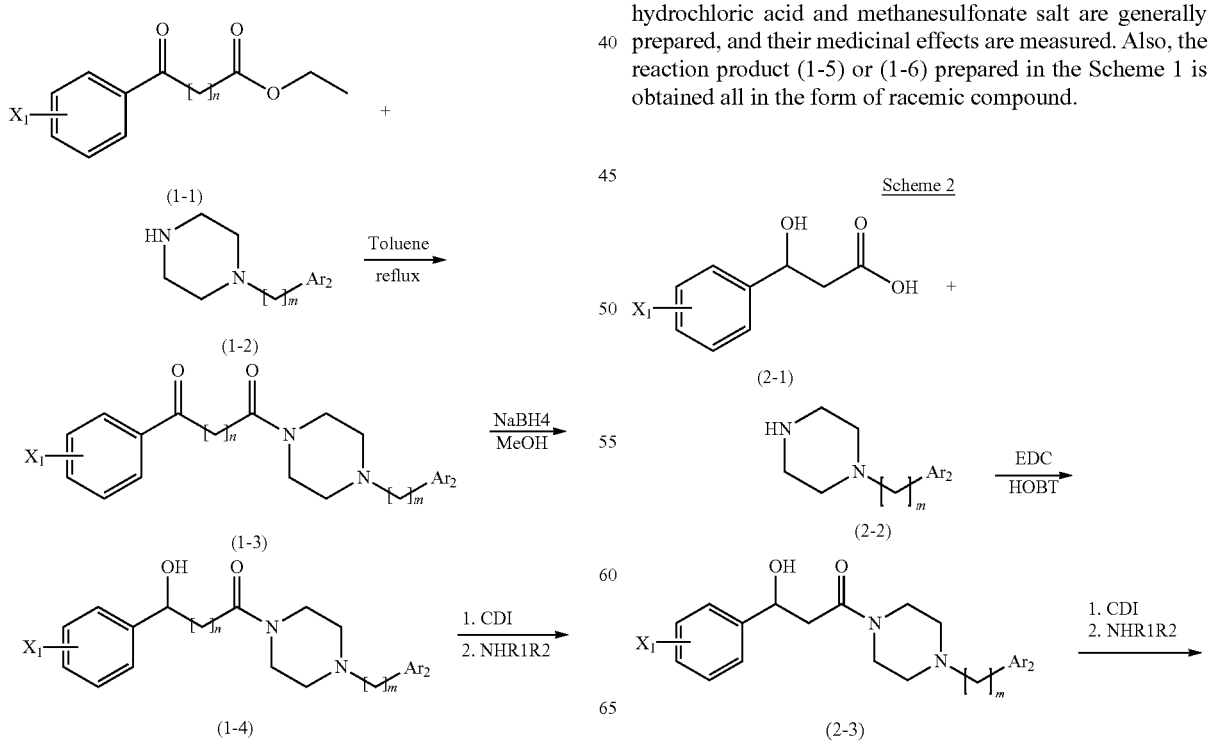

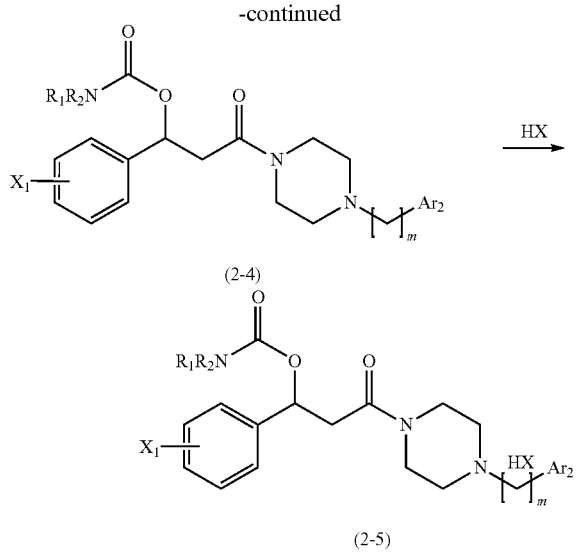

As shown in the Scheme 2, 3-hydroxy-3-phenylpropionic acid substituted by $X_1$ and a phenylpiperazine compound (2-2) are subject to a binding reaction at the presence of 1-ethyl-3-(3-dimethylaminopropyl)carbodiimide/1-hydroxy benzotriazole (EDC/HOBT) to synthesize an amide compound (2-3). The amide compound (2-3) is reacted with 1,1-carbonyldiimidazole (CDI), and then reacted with various amines ($NHR_1R_2$) to obtain a compound (2-4) and its salt (2-5).

The stereochemistry of the reaction product (2-5) depends only on the starting material (2-1); that is, a reaction product having an (S)-enantiomer only is obtained from the starting material (2-1) having an (S)-enantiomer, and a reaction product having a (R)-enantiomer only is obtained from the starting material (2-1) having a (R)-enantiomer.

According to the present invention, there is provided a pharmaceutical composition including an effective amount of the compound to treat pain, anxiety or depression. Here, the pharmaceutical composition includes, as an active component, at least one compound among the compounds as listed in this application, and the composition according to the present invention may include any combination of the compounds according to the present invention.

The pharmaceutical composition of present invention may be specifically formulated so that it can be administered via any form, such as suitable routes of administration. Here, the suitable routes of administration may, for example, include oral, rectal, nasal, pulmonary, local, percutaneous, intracisternal, intraperitoneal, vaginal, and parenteral (including subcutaneous, intramuscular, intrathecal, intravenous and transdermal routes) routes. The pharmaceutical composition of present invention is preferably administered via the oral route. The preferred routes of administration will, of course, be varied depending on a variety of factors, including the general conditions and age of the subject being treated, the severity of the conditions being treated, and the selected active components, etc.

Pharmaceutical preparations formulated according to the present invention may be administered orally in any form of administration, such as suitable forms of a tablet, a capsule, a powder, a granule, a pellet, a troche, a dragee, a pill or lozenge, a solution or suspension in an aqueous or non-aqueous liquid, or an oil-in-water or water-in-oil liquid emulsion, an elixir, a syrup, etc., or be administered parenterally in the form of injections. Other pharmaceutical compositions that may be administered parenterally include a dispersion, a suspension and an emulsion, as well as sterile powders included in a sterile injection solution or dispersion before their use. It is considered that a depot injection formulation is also included within the scope of the present invention. Other suitable forms of administration include a suppository, a spray, an ointment, a cream, a gelatin, an inhalant, a skin patch, etc. The composition according to the present invention may be formulated according to various methods known in the art. Also, pharmaceutically available carrier, diluent, excipient or other additives, which are used in general in the art, may be used herein.

The carrier that which generally used in formulations includes, but is not particularly limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxy benzoate, talc, magnesium stearate, mineral oil, etc. The composition of the present invention may further includes a preservative, a stability-improving compound, a viscosity-improving/regulating compound, a solubility-improving compound, a sweetener, a dye, a taste-enhancing compound, an osmosis-inducing salt, a buffer, an antioxidant, etc.

Where the above-mentioned compounds show a desired effect to treat pain, anxiety or depression, the compounds may be used in the form of solvates, esters, stereoisomers, etc. including free compounds, pharmaceutically available salts and hydrates. Also, the above-mentioned compounds are all included in the scope of the present invention.

According to the present invention, the pharmaceutically available salts may include pharmaceutically available acid addition salts. The pharmaceutically available acid addition salts may be obtained from inorganic acids such as hydrochloric acid, nitric acid, phosphoric acid, sulfuric acid, hydrobromic acid, hydriodic acid, nitrous acid and phosphorous acid; and non-toxic organic acids such as aliphatic mono and di-carboxylate, phenyl-substituted alkanoate, hydroxy alkanoate and alkandioate, aromatic acids, aliphatic and aromatic sulfonic acids; and the like. Specific examples of the pharmaceutically available salts includes, but is not particularly limited to, sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propionate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, maleate, tartrate, methane sulfonate, propanesulfonate, naphthalene-1-sulfonate, naphthalene-2-sulfonate and mandelate. Particularly, hydrochloric acid and methane sulfonate are preferred.

The present invention provides a method for treating pain, anxiety or depression in mammals, characterized in that an effective amount of the compound is administered to the mammals in need of treatment thereof.

The pain, which may be treated by the compound of the present invention, includes a wide range of pains such as acute pain, chronic pain, neuropathic pain, post-surgery neuropathic pain, diabetic neuropathic pain, postherpetic neuralgia, inflammatory pain, joint pain, migraine headache and the like, anxiety and depression.

In general, the pharmaceutical composition of the present invention is administered with an active component at a unit dose ranging from approximately 20 to 500 mg. The total daily dose may be generally administered at the amount ranging from approximately 10 to 7000 mg, and preferably from 20 to 3500 mg of the active compound of the present invention. However, the active compound may also be administered at a certain amount out of the dose range under general investigation of the conditions of patients, and also in consideration of the activity of agents to be administered. In this case, the optimum dose amount of such agents in the particular conditions should be determined by routine experimentations.

The compound of the present invention may be administered in single or multiple daily doses, and the dose of the compound may be preferably divided into one to four times per day. The compound of the present invention may be administered alone or in combination of a pharmaceutically available carrier or an excipient. The pharmaceutical composition according to the present invention may be formulated in a pharmaceutically available carrier or a diluent, as well as in a supplement and an excipient that are widely known in the art. For convenience' sake, the formulations may be present in dosages suitable for such administration by using the methods known in the field of pharmacology.

MODE FOR THE INVENTION

Hereinafter, exemplary embodiments of the present invention will be described in detail. However, it should be understood that the description proposed herein is just a preferable example for the purpose of illustrations only, not intended to limit the scope of the invention.

1. Synthesis of Carbamoyloxy Arylalkanoyl Arylpiperazine Compounds

Example 1

Carbamic acid 3-[4-(4-fluoro-phenyl)-piperazin-1-yl]-3-oxo-1-phenyl-propyl ester Ethyl benzoylacetate (2.887 mmol) and 4-fluorophenylpiperazine (2.887 mmol) were dissolved in toluene, and refluxed for 24 hours. The resulting reaction mixture was concentrated under a reduced pressure, and dissolved in methanol, and cooled to 0° C., and sodium borohydride (2.887 mmol) was then added dropwise to the resulting mixture. The resulting mixture was stirred at a room temperature for 2 hours, concentrated under a reduced pressure, diluted with water, and then extracted several times with ethyl acetate to obtain an organic phase. The resulting organic phase was dried over magnesium sulfate, filtered, and then concentrated under a reduced pressure. The resulting mixture was purified with column chromatography (hexane:ethyl acetate=1:1) to obtain a compound. The prepared compound was dissolved in tetrahydrofuran (10 mL), and 1,1'-carbodiimidazole (5 mmol) was added to the resulting mixture. Then, the resulting mixture was stirred at a room temperature for 1 hour, and excessive ammonium hydroxide was added to the reaction mixture. The resulting reaction mixture was stirred at a room temperature for 1 hour. The reaction mixture was diluted with water, and extracted several times with ethyl acetate to obtain an organic phase. The prepared organic phase was dried over magnesium sulfate, filtered, and then concentrated under a reduced pressure. The resulting pellet was purified with column chromatography (ethyl acetate) to obtain a title compound.

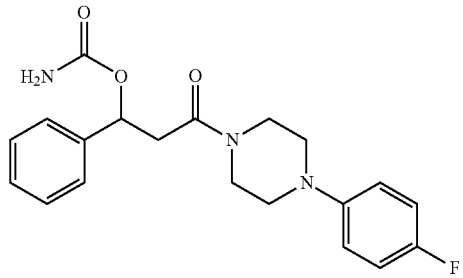 [SMILES: NC(=O)OC(CC(=O)N1CCN(c2ccc(F)cc2)CC1)c1ccccc1]

$^1$H NMR (200 MHz, CDCl3) d: 2.82 (dd, 1H), 3.03 (m, 5H), 3.60 (m, 2H), 3.76 (m, 2H), 4.73 (br, 2H), 6.16 (t, 1H), 6.95 (m, 4H), 7.38 (m, 5H)

Compounds of Examples 2 to 60 were prepared in the same manner as in the Example 1, except that the different starting materials were used in the Examples 2 to 60.

Example 2

Carbamic acid 3-[4-(4-methoxy-phenyl)-piperazin-1-yl]-3-oxo-1-phenyl-propyl ester A title compound was prepared in the same manner as in Example 1 except for the use of ethyl benzoylacetate and 4-methoxyphenylpiperazine.

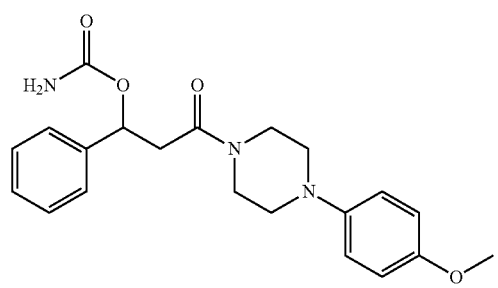 [SMILES: COc1ccc(N2CCN(C(=O)CC(OC(N)=O)c3ccccc3)CC2)cc1]

$^1$H NMR (200 MHz, CDCl3) d: 3.00 (m, 6H), 3.60 (m, 2H), 3.79 (m, 5H), 4.82 (br, 2H), 6.18 (t, 1H), 6.88 (m, 4H), 7.38 (m, 5H).

Example 3

Carbamic acid 3-[4-(3,4-dichloro-phenyl)-piperazin-1-yl]-3-oxo-1-phenyl-propyl ester A title compound was prepared in the same manner as in Example 1 except for the use of ethyl benzoylacetate and 3,4-dichlorophenylpiperazine.

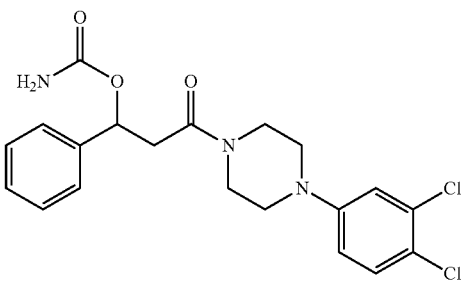 [SMILES: NC(=O)OC(CC(=O)N1CCN(c2ccc(Cl)c(Cl)c2)CC1)c1ccccc1]

$^1$H NMR (200 MHz, CDCl3) d: 2.82 (dd, 1H), 3.09 (m, 5H), 3.58 (m, 2H), 3.74 (m, 2H), 4.81 (br, 2H), 6.14 (t, 1H), 6.73 (dd, 1H), 6.94 (d, 1H), 7.40 (m, 6H)

Example 4

Carbamic acid 3-oxo-1-phenyl-3-(4-p-tolyl-piperazin-1-yl)-propyl ester

A title compound was prepared in the same manner as in Example 1 except for the use of ethyl benzoylacetate and 4-methylphenylpiperazine.

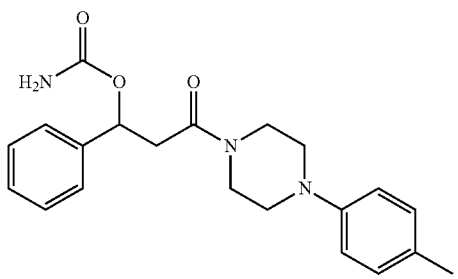

$^1$H NMR (200 MHz, CDCl3) d: 2.30 (s, 3H), 2.82 (dd, 1H), 3.05 (m, 5H), 3.60 (m, 2H), 3.77 (m, 2H), 4.77 (br, 2H), 6.15 (t, 1H), 6.84 (d, 2H), 7.10 (d, 2H), 7.38 (m, 5H)

Example 5

Carbamic acid 3-[4-(3,4-dimethoxy-phenyl)-piperazin-1-yl]-3-oxo-1-phenyl-propyl ester A title compound was prepared in the same manner as in Example 1 except for the use of ethyl benzoylacetate and 3,4-dimethoxyphenylpiperazine.

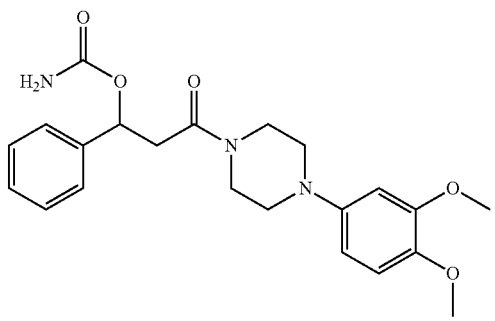

$^1$H NMR (200 MHz, CDCl3) d: 2.82 (dd, 1H), 3.04 (m, 5H), 3.61 (m, 2H), 3.77 (m, 2H), 3.88 (d, 6H), 4.77 (br, 2H), 6.15 (t, 1H), 6.42 (d, 1H), 6.57 (s, 1H), 6.82 (d, 1H), 7.41 (m, 5H)

Example 6

Carbamic acid 1-(4-chloro-phenyl)-3-[4-(3,4-dimethoxy-phenyl)-piperazin-1-yl]-3-oxo-propyl ester A title compound was prepared in the same manner as in Example 1 except for the use of ethyl-4-chloro-benzoylacetate and 3,4-dimethoxyphenylpiperazine.

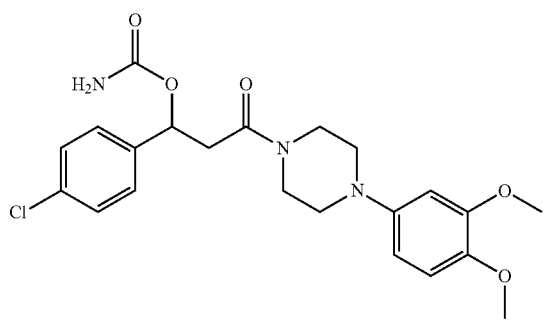 [SMILES: COc1ccc(N2CCN(C(=O)CC(OC(N)=O)c3ccc(Cl)cc3)CC2)cc1OC]

$^1$H NMR (200 MHz, CDCl3) d: 2.82 (dd, 1H), 3.01 (m, 5H), 3.61 (m, 2H), 3.77 (m, 2H), 3.86 (d, 6H), 4.84 (br, 2H), 6.15 (t, 1H), 6.42 (d, 1H), 6.57 (s, 1H), 6.82 (d, 1H), 7.35 (s, 4H)

Example 7

Carbamic acid 3-[4-(3,4-dimethoxy-phenyl)-piperazin-1-yl]-1-(4-fluoro-phenyl)-3-oxo-propyl ester A title compound was prepared in the same manner as in Example 1 except for the use of ethyl-4-fluoro-benzoylacetate and 3,4-dimethoxyphenylpiperazine.

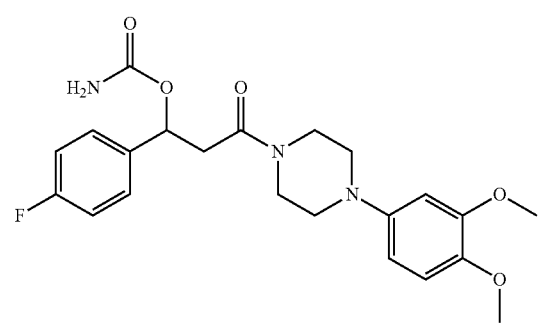 [SMILES: COc1ccc(N2CCN(C(=O)CC(OC(N)=O)c3ccc(F)cc3)CC2)cc1OC]

$^1$H NMR (200 MHz, CDCl3) d: 2.82 (dd, 1H), 3.01 (m, 5H), 3.60 (m, 2H), 3.75 (m, 2H), 3.86 (d, 6H), 4.92 (br, 2H), 6.15 (t, 1H), 6.42 (d, 1H), 6.56 (d, 1H), 6.80 (d, 1H), 7.04 (t, 2H), 7.38 (t, 2H)

Example 8

Carbamic acid 3-[4-(3,4-dimethoxy-phenyl)-piperazin-1-yl]-3-oxo-1-p-tolyl-propyl ester A title compound was prepared in the same manner as in Example 1 except for the use of ethyl-4-methyl-benzoylacetate and 3,4-dimethoxyphenylpiperazine.

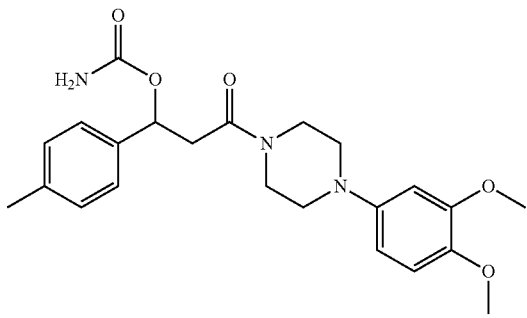

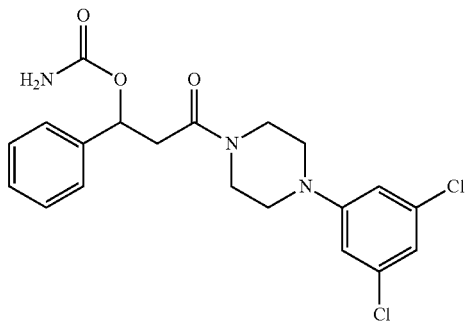

¹H NMR (200 MHz, CDCl3) d: 2.35 (s, 3H), 2.82 (dd, 1H), 3.04 (m, 5H), 3.62 (m, 2H), 3.77 (m, 2H), 3.88 (d, 6H), 4.67 (br, 2H), 6.11 (t, 1H), 6.47 (dd, 1H), 6.58 (d, 1H), 6.81 (d, 1H), 7.18 (d, 2H), 7.32 (d, 2H)

¹H NMR (200 MHz, CDCl3) d: 2.82 (dd, 1H), 3.13 (m, 5H), 3.56 (m, 2H), 3.75 (m, 2H), 4.76 (br, 2H), 6.14 (t, 1H), 6.73 (m, 2H), 6.86 (m, 1H), 7.39 (m, 5H)

Example 9

Carbamic acid 3-[4-(2,4-dimethoxy-phenyl)-piperazin-1-yl]-3-oxo-1-phenyl-propyl ester A title compound was prepared in the same manner as in Example 1 except for the use of ethyl benzoylacetate and 2,4-dimethoxyphenylpiperazine.

Example 11

Carbamic acid 3-[4-(3,5-dimethoxy-phenyl)-piperazin-1-yl]-3-oxo-1-phenyl-propyl ester A title compound was prepared in the same manner as in Example 1 except for the use of ethyl benzoylacetate and 3,5-dimethoxyphenylpiperazine.

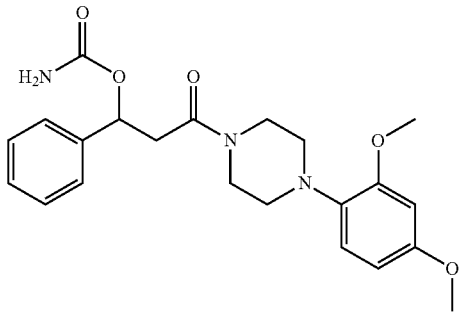 [SMILES: COc1ccc(N2CCN(C(=O)CC(OC(N)=O)c3ccccc3)CC2)c(OC)c1]

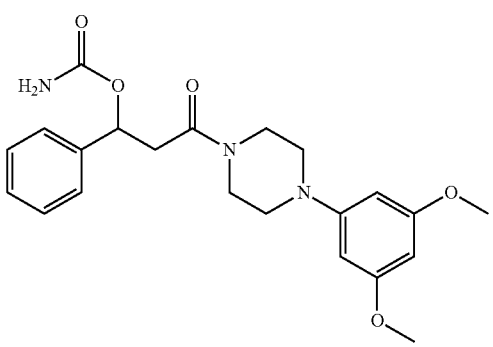 [SMILES: COc1cc(OC)cc(N2CCN(C(=O)CC(OC(N)=O)c3ccccc3)CC2)c1]

¹H NMR (200 MHz, CDCl3) d: 2.89 (m, 6H), 3.59 (m, 2H), 3.82 (m, 8H), 4.98 (br, 2H), 6.12 (t, 1H), 6.42 (dd, 1H), 6.49 (d, 1H), 6.79 (d, 1H), 7.35 (m, 5H)

¹H NMR (200 MHz, CDCl3) d: 2.82 (dd, 1H), 3.11 (m, 5H), 3.56 (m, 2H), 3.80 (m, 8H), 4.79 (br, 2H), 6.08 (m, 4H), 7.39 (m, 5H)

Example 10

Carbamic acid 3-[4-(3,5-dichloro-phenyl)-piperazin-1-yl]-3-oxo-1-phenyl-propyl ester A title compound was prepared in the same manner as in Example 1 except for the use of ethyl benzoylacetate and 3,5-dichlorophenylpiperazine.

Example 12

Carbamic acid 3-[4-(2,3-dichloro-phenyl)-piperazin-1-yl]-3-oxo-1-phenyl-propyl ester A title compound was prepared in the same manner as in Example 1 except for the use of ethyl benzoylacetate and 2,3-dichlorophenylpiperazine.

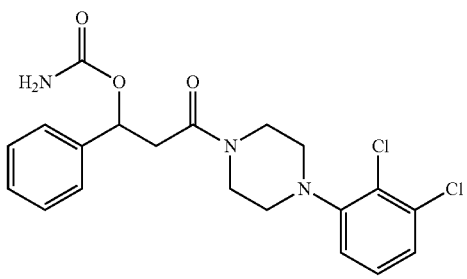 [SMILES: NC(=O)OC(CC(=O)N1CCN(c2cccc(Cl)c2Cl)CC1)c1ccccc1]

¹H NMR (200 MHz, CDCl3) d: 2.96 (m, 6H), 3.62 (m, 2H), 3.80 (m, 2H), 4.73 (br, 2H), 6.16 (t, 1H), 6.88 (dd, 1H), 7.31 (m, 7H)

Example 13

Carbamic acid 3-[4-(2,4-difluoro-phenyl)-piperazin-1-yl]-3-oxo-1-phenyl-propyl ester A title compound was prepared in the same manner as in Example 1 except for the use of ethyl benzoylacetate and 2,4-difluorophenylpiperazine.

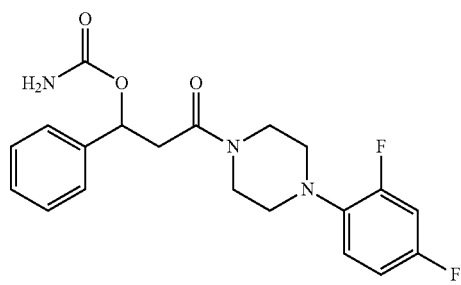 [SMILES: NC(=O)OC(CC(=O)N1CCN(c2ccc(F)cc2F)CC1)c1ccccc1]

¹H NMR (200 MHz, CDCl3) d: 2.95 (m, 6H), 3.61 (m, 2H), 3.80 (m, 2H), 4.69 (br, 2H), 6.15 (t, 1H), 6.82 (m, 3H), 7.35 (m, 5H)

Example 14

Carbamic acid 3-(4-benzo[1,3]dioxol-5-yl-piperazin-1-yl)-3-oxo-1-phenyl-propyl ester A title compound was prepared in the same manner as in Example 1 except for the use of ethyl benzoylacetate and 3,4-methylenedioxyphenylpiperazine.

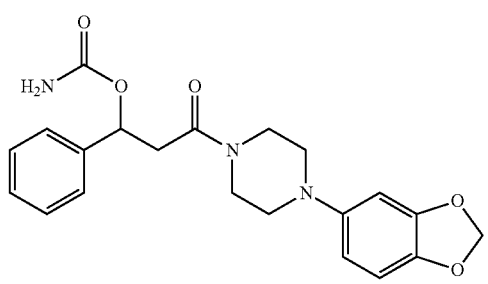 [SMILES: NC(=O)OC(CC(=O)N1CCN(c2ccc3c(c2)OCO3)CC1)c1ccccc1]

¹H NMR (200 MHz, CDCl3) d: 2.98 (m, 6H), 3.59 (m, 2H), 3.76 (m, 2H), 4.71 (br, 2H), 5.94 (s, 2H), 6.15 (t, 1H), 6.36 (dd, 1H), 6.55 (s, 1H), 6.74 (d, 1H), 3.40 (m, 5H)

Example 15

Carbamic acid 1-(4-methoxy-phenyl)-3-oxo-3-(4-phenyl-piperazin-1-yl)-propyl ester A title compound was prepared in the same manner as in Example 1 except for the use of ethyl-4-methoxy-benzoylacetate and phenylpiperazine.

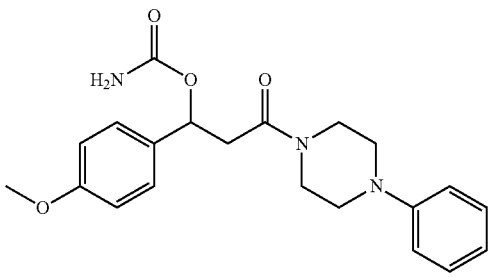 [SMILES: COc1ccc(C(CC(=O)N2CCN(c3ccccc3)CC2)OC(N)=O)cc1]

¹H NMR (200 MHz, CDCl3) d: 2.82 (dd, 1H), 3.11 (m, 5H), 3.60 (m, 2H), 3.74 (m, 2H), 3.78 (s, 3H), 5.01 (br, 2H), 6.08 (t, 1H), 6.91 (m, 5H), 7.33 (m, 4H)

Example 16

Carbamic acid 1-(4-chloro-phenyl)-3-oxo-3-(4-phenyl-piperazin-1-yl)-propyl ester A title compound was prepared in the same manner as in Example 1 except for the use of ethyl-4-chloro-benzoylacetate and phenylpiperazine.

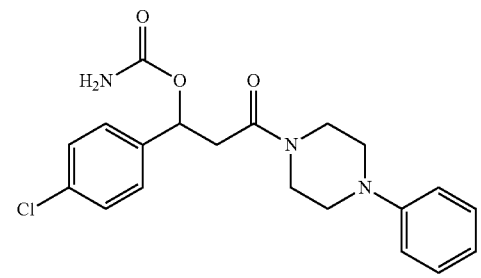 [SMILES: NC(=O)OC(CC(=O)N1CCN(c2ccccc2)CC1)c1ccc(Cl)cc1]

¹H NMR (200 MHz, CDCl3) d: 2.82 (dd, 1H), 3.14 (m, 5H), 3.60 (m, 2H), 3.74 (m, 2H), 4.81 (br, 2H), 6.12 (t, 1H), 6.94 (m, 3H), 7.33 (m, 6H)

Example 17

Carbamic acid 3-[4-(4-tert-butyl-phenyl)-piperazin-1-yl]-3-oxo-1-phenyl-propyl ester A title compound was prepared in the same manner as in Example 1 except for the use of ethyl benzoylacetate and 4-tert-butylphenylpiperazine.

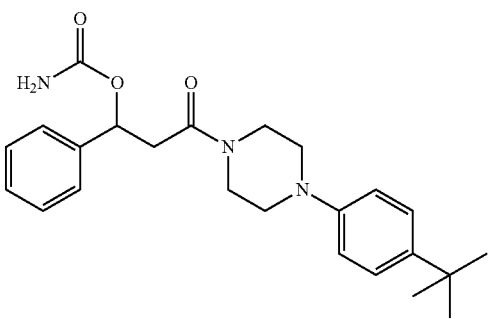 [SMILES: CC(C)(C)c1ccc(N2CCN(C(=O)CC(OC(N)=O)c3ccccc3)CC2)cc1]

¹H NMR (200 MHz, CDCl3) d: 1.32 (s, 9H), 2.82 (dd, 1H), 3.08 (m, 5H), 3.60 (m, 2H), 3.76 (m, 2H), 4.68 (br, 2H), 6.18 (t, 1H), 6.94 (m, 2H), 7.35 (m, 7H)

Example 18

Carbamic acid 3-[4-(4-hydroxy-phenyl)-piperazin-1-yl]-3-oxo-1-phenyl-propyl ester A title compound was prepared in the same manner as in Example 1 except for the use of ethyl benzoylacetate and 4-hydroxyphenylpiperazine.

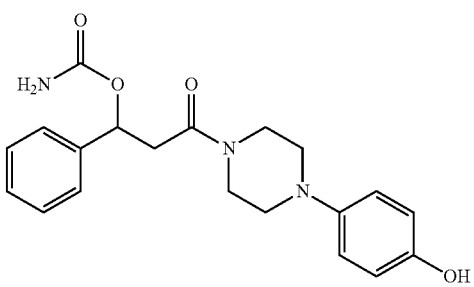

¹H NMR (200 MHz, DMSO) d: 2.82 (m, 6H), 3.56 (m, 4H), 5.93 (t, 1H), 6.51 (br, 2H), 6.67 (d, 2H), 6.78 (d, 2H), 7.37 (m, 5H), 8.88 (s, 1H)

Example 19

Dimethyl-carbamic acid 3-[4-(4-methoxy-phenyl)-piperazin-1-yl]-3-oxo-1-phenyl-propyl ester Ethyl benzoylacetate (2 mmol) and 4-methoxyphenylpiperazine (2 mmol) were dissolved in toluene, and refluxed for 24 hours. The resulting mixture was concentrated under a reduced pressure to obtain a crude compound, and the crude compound was dissolved in methanol, and cooled to 0° C. Then, sodium borohydride (2 mmol) was added dropwise to the resulting mixture. The mixture was stirred at a room temperature for 2 hours, concentrated under a reduced pressure, diluted with water, and then extracted several times with ethyl acetate to obtain an organic phase. The prepared organic phase was dried over magnesium sulfate, filtered, and then concentrated under a reduced pressure. The resulting pellet was purified with column chromatography (hexane:ethyl acetate=1:1) to obtain a compound. The prepared compound was dissolved in tetrahydrofuran (8 mL), and 1,1'-carbodiimidazole (4 mmol) was added to the resulting mixture. Then, the resulting mixture was stirred at a room temperature for 1 hour, and excessive dimethylamine was added to the reaction mixture. The resulting reaction mixture was stirred at a room temperature for 1 hour. The reaction mixture was diluted with water, and extracted several times with ethyl acetate to obtain an organic phase. The prepared organic phase was dried over magnesium sulfate, filtered, and then concentrated under a reduced pressure. The resulting pellet was purified with column chromatography (ethyl acetate) to obtain a title compound.

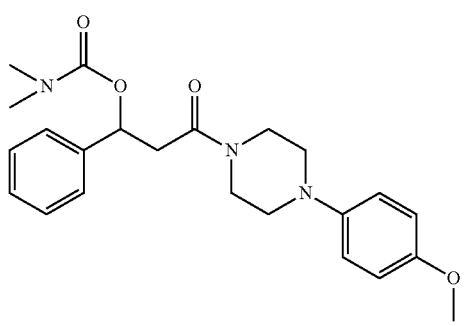 [SMILES: COc1ccc(N2CCN(C(=O)CC(OC(=O)N(C)C)c3ccccc3)CC2)cc1]

¹H NMR (200 MHz, CDCl3) d: 2.95 (m, 12H), 3.60 (m, 2H), 3.74 (m, 2H), 3.78 (s, 3H), 6.18 (t, 1H), 6.87 (m, 4H), 7.39 (m, 5H)

Example 20

Carbamic acid 3-[4-(3,4-dimethyl-phenyl)-piperazin-1-yl]-3-oxo-1-phenyl-propyl ester A title compound was prepared in the same manner as in Example 1 except for the use of ethyl benzoylacetate and 3,4-dimethylphenylpiperazine.

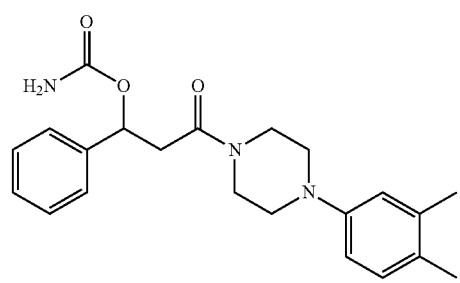 [SMILES: Cc1ccc(N2CCN(C(=O)CC(OC(N)=O)c3ccccc3)CC2)cc1C]

¹H NMR (200 MHz, CDCl3) d: 2.21 (s, 3H), 2.26 (s, 3H), 2.83 (dd, 1H), 3.07 (m, 5H), 3.59 (m, 2H), 3.75 (m, 2H), 4.72 (br, 2H), 6.18 (t, 1H), 6.68 (d, 1H), 6.74 (s, 1H), 7.05 (d, 1H), 7.38 (m, 5H)

Example 21

Carbamic acid 3-{4-[bis-(4-fluoro-phenyl)-methyl]-piperazin-1-yl}-3-oxo-1-phenyl-propyl ester A title compound was prepared in the same manner as in Example 1 except for the use of ethyl benzoylacetate and 4,4'-difluorobisphenylpiperazine.

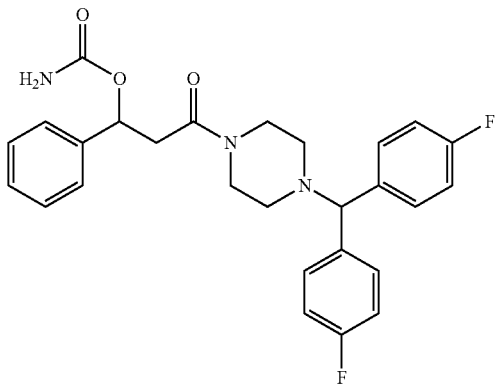 [SMILES: NC(=O)OC(CC(=O)N1CCN(C(c2ccc(F)cc2)c2ccc(F)cc2)CC1)c1ccccc1]

¹H NMR (200 MHz, CDCl3) d: 2.30 (m, 4H), 2.75 (dd, 1H), 2.97 (dd, 1H), 3.44 (m, 2H), 3.59 (m, 2H), 4.21 (s, 1H), 4.99 (br, 2H), 6.07 (t, 1H), 6.99 (t, 4H), 7.33 (m, 9H)

Example 22

Carbamic acid 3-oxo-1-phenyl-3-(4-quinoxalin-2-yl-piperazin-1-yl)-propyl ester

A title compound was prepared in the same manner as in Example 1 except for the use of ethyl benzoylacetate and 2-piperazin-1-yl-quinoxaline.

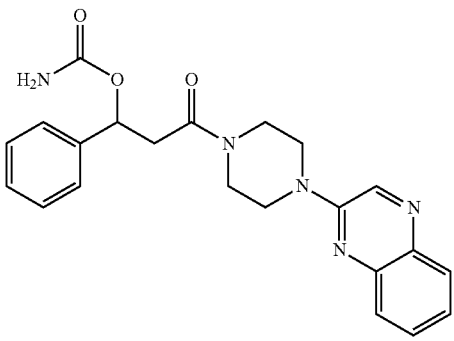 [SMILES: NC(=O)OC(CC(=O)N1CCN(c2cnc3ccccc3n2)CC1)c1ccccc1]

¹H NMR (200 MHz, CDCl3) d: 2.82 (dd, 1H), 3.10 (dd, 1H), 3.77 (m, 8H), 4.71 (br, 2H), 6.15 (t, 1H), 7.42 (m, 6H), 7.71 (m, 2H), 7.94 (d, 1H), 8.59 (s, 1H)

Example 23

Acetic acid 4-[4-(3-carbamoyloxy-3-phenyl-propionyl)-piperazin-1-yl]-phenyl ester The compound 'carbamic acid 3-[4-(4-hydroxy-phenyl)-piperazin-1-yl]-3-oxo-1-phenyl-propyl este (2 mmol)' prepared in Example 18 was dissolved in tetrahydrofuran 25 mL), and triethylamine (2.4 mmol) and acetylchloride (2.4 mmol) were added to the mixture. The resulting mixture was stirred at a room temperature for 5 hours. Then, the reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1) to obtain a title compound.

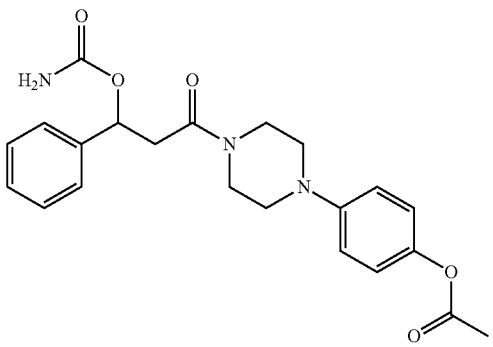 [SMILES: CC(=O)Oc1ccc(N2CCN(C(=O)CC(OC(N)=O)c3ccccc3)CC2)cc1]

¹H NMR (200 MHz, CDCl3) d: 2.28 (s, 3H), 2.80 (dd, 1H), 3.04 (m, 5H), 3.58 (m, 2H), 3.72 (m, 2H), 4.95 (br, 2H), 6.12 (t, 1H), 6.87 (d, 2H), 7.00 (d, 2H), 7.38 (m, 5H)

Example 24

Carbamic acid 3-oxo-1-phenyl-3-(4-pyridin-2-yl-piperazin-1-yl)-propyl ester

A title compound was prepared in the same manner as in Example 1 except for the use of ethyl benzoylacetate and 2-piperazin-1-yl-pyridine.

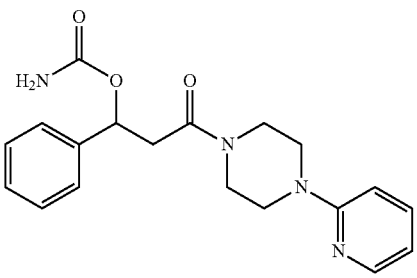 [SMILES: NC(=O)OC(CC(=O)N1CCN(c2ccccn2)CC1)c1ccccc1]

¹H NMR (200 MHz, CDCl3) d: 2.83 (dd, 1H), 3.10 (dd, 1H), 3.50 (6, 2H), 3.72 (m, 2H), 4.76 (br, 2H), 6.16 (t, 1H), 6.67 (m, 2H), 7.41 (m, 6H), 8.20 (m, 1H)

Example 25

Carbamic acid 3-oxo-1-phenyl-3-(4-pyrimidin-2-yl-piperazin-1-yl)-propyl ester

A title compound was prepared in the same manner as in Example 1 except for the use of ethyl benzoylacetate and 2-piperazin-1-yl-pyrimidine.

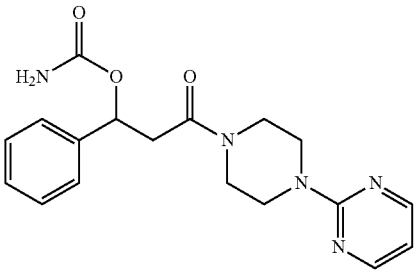 [SMILES: NC(=O)OC(CC(=O)N1CCN(c2ncccn2)CC1)c1ccccc1]

¹H NMR (200 MHz, CDCl3) d: 2.84 (dd, 1H), 3.09 (dd, 1H), 3.51 (m, 2H), 3.76 (m, 6H), 4.73 (br, 2H), 6.16 (t, 1H), 6.55 (t, 1H), 7.41 (m, 5H), 8.33 (d, 2H)

Example 26

Carbamic acid 3-[4-(3,5-dichloro-pyridin-2-yl)-piperazin-1-yl]-3-oxo-1-phenyl-propyl ester A title compound was prepared in the same manner as in Example 1 except for the use of ethyl benzoylacetate and 1-(3,5-dichloro-pyridine-2-yl)piperazine.

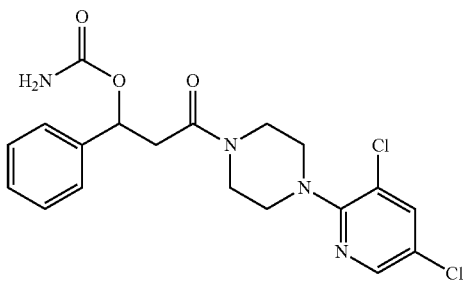 [SMILES: NC(=O)OC(CC(=O)N1CCN(c2ncc(Cl)cc2Cl)CC1)c1ccccc1]

¹H NMR (200 MHz, CDCl3) d: 2.82 (dd, 1H), 3.09 (dd, 1H), 3.28 (m, 4H), 3.60 (m, 2H), 3.75 (m, 2H), 4.89 (br, 2H), 6.13 (t, 1H), 7.39 (m, 5H), 7.63 (s, 1H), 8.13 (s, 1H)

Example 27

Carbamic acid 3-[4-(4-chloro-3-trifluoromethyl-phenyl)-piperazin-1-yl]-3-oxo-1-phenyl-propyl ester A title compound was prepared in the same manner as in Example 1 except for the use of ethyl benzoylacetate and 3-chloro-4-trifluoromethylphenylpiperazine.

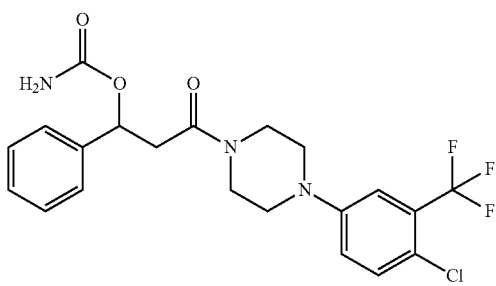 [SMILES: NC(=O)OC(CC(=O)N1CCN(c2ccc(Cl)c(C(F)(F)F)c2)CC1)c1ccccc1]

¹H NMR (200 MHz, CDCl3) d: 2.86 (dd, 1H), 3.11 (m, 5H), 3.60 (m, 2H), 3.74 (m, 2H), 4.75 (br, 2H), 6.16 (t, 1H), 6.96 (dd, 1H), 7.15 (d, 1H), 7.40 (m, 6H)

Example 28

Carbamic acid 3-oxo-1-phenyl-3-[4-(4-trifluoromethyl-phenyl)-piperazin-1-yl]-propyl ester A title compound was prepared in the same manner as in Example 1 except for the use of ethyl benzoylacetate and 4-trifluoromethylphenylpiperazine.

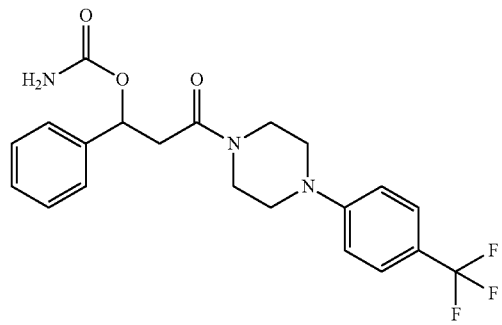 [SMILES: NC(=O)OC(CC(=O)N1CCN(c2ccc(C(F)(F)F)cc2)CC1)c1ccccc1]

¹H NMR (200 MHz, CDCl3) d: 2.82 (dd, 1H), 3.24 (m, 5H), 3.62 (m, 2H), 3.78 (m, 2H), 4.65 (br, 2H), 6.18 (t, 1H), 6.92 (d, 2H), 7.41 (m, 5H), 7.52 (d, 2H)

Example 29

Carbamic acid 3-[4-(2-fluoro-phenyl)-piperazin-1-yl]-3-oxo-1-phenyl-propyl ester A title compound was prepared in the same manner as in Example 1 except for the use of ethyl benzoylacetate and 2-fluorophenylpiperazine.

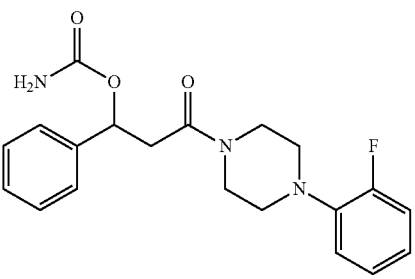 [SMILES: NC(=O)OC(CC(=O)N1CCN(c2ccccc2F)CC1)c1ccccc1]

¹H NMR (200 MHz, CDCl3) d: 2.84 (dd, 1H), 3.04 (m, 5H), 3.62 (m, 2H), 3.78 (m, 2H), 4.76 (br, 2H), 6.16 (t, 1H), 7.04 (m, 4H), 7.39 (m, 5H)

Example 30

Carbamic acid 3-[4-(3-fluoro-phenyl)-piperazin-1-yl]-3-oxo-1-phenyl-propyl ester A title compound was prepared in the same manner as in Example 1 except for the use of ethyl benzoylacetate and 3-fluorophenylpiperazine.

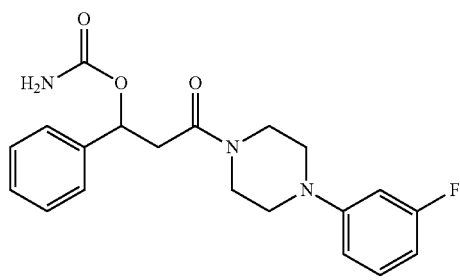 [SMILES: NC(=O)OC(CC(=O)N1CCN(c2cccc(F)c2)CC1)c1ccccc1]

¹H NMR (200 MHz, CDCl3) d: 2.84 (dd, 1H), 3.13 (m, 5H), 3.59 (m, 2H), 3.77 (m, 2H), 4.78 (br, 2H), 6.14 (t, 1H), 6.62 (m, 3H), 7.21 (m, 1H), 7.41 (m, 5H)

Example 31

Carbamic acid 3-oxo-3-(4-phenyl-piperazin-1-yl)-1-(4-trifluoromethyl-phenyl)-propyl ester A title compound was prepared in the same manner as in Example 1 except for the use of ethyl-4-trifluoromethyl-benzoylacetate and phenylpiperazine.

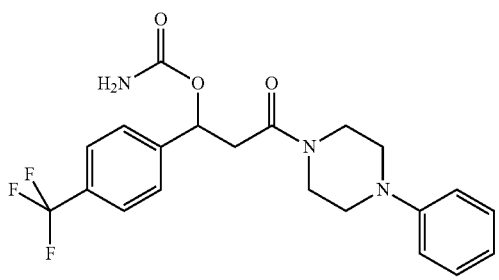 [SMILES: NC(=O)OC(CC(=O)N1CCN(c2ccccc2)CC1)c1ccc(C(F)(F)F)cc1]

¹H NMR (200 MHz, CDCl3) d: 2.84 (m, 1H), 3.13 (m, 5H), 3.62 (m, 2H), 3.78 (m, 2H), 4.92 (br, 2H), 6.22 (t, 1H), 6.92 (m, 3H), 7.31 (m, 2H), 7.63 (m, 4H)

Example 32

Carbamic acid 3-oxo-3-(4-phenyl-piperazin-1-yl)-1-p-tolyl-propyl ester

A title compound was prepared in the same manner as in Example 1 except for the use of ethyl-4-methyl-benzoylacetate and phenylpiperazine.

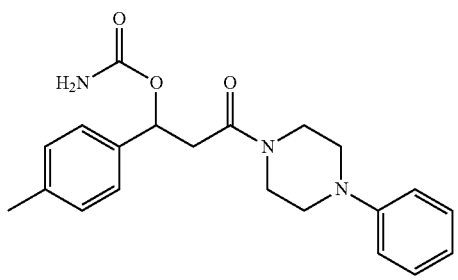 [SMILES: Cc1ccc(C(CC(=O)N2CCN(c3ccccc3)CC2)OC(N)=O)cc1]

¹H NMR (200 MHz, CDCl3) d: 2.82 (dd, 1H), 3.11 (m, 5H), 3.62 (m, 2H), 3.77 (m, 2H), 4.71 (br, 2H), 6.12 (t, 1H), 6.93 (m, 3H), 7.30 (m, 6H)

Example 33

Carbamic acid 3-[4-(3,4-difluoro-phenyl)-piperazin-1-yl]-3-oxo-1-phenyl-propyl ester A title compound was prepared in the same manner as in Example 1 except for the use of ethyl benzoylacetate and 3,4-difluoro phenylpiperazine.

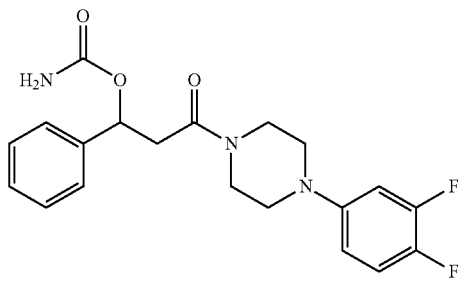 [SMILES: NC(=O)OC(CC(=O)N1CCN(c2ccc(F)c(F)c2)CC1)c1ccccc1]

¹H NMR (200 MHz, CDCl3) d: 2.82 (dd, 1H), 3.03 (m, 5H), 3.59 (m, 2H), 3.76 (m, 2H), 4.76 (br, 2H), 6.14 (t, 1H), 6.68 (m, 2H), 7.05 (q, 1H), 7.40 (m, 5H)

Example 34

Carbamic acid 1-(4-nitro-phenyl)-3-oxo-3-(4-phenylpiperazin-1-yl)-propyl ester

A title compound was prepared in the same manner as in Example 1 except for the use of ethyl-4-nitro-benzoylacetate and phenylpiperazine.

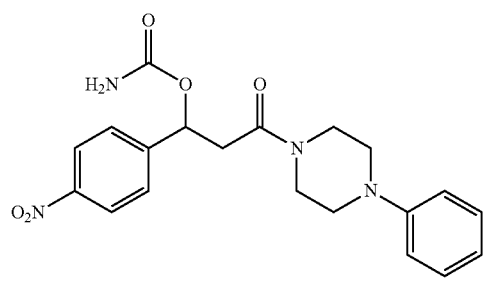 [SMILES: NC(=O)OC(CC(=O)N1CCN(c2ccccc2)CC1)c1ccc([N+](=O)[O-])cc1]

¹H NMR (200 MHz, CDCl3) d: 2.82 (dd, 1H), 3.15 (m, 5H), 3.59 (m, 2H), 3.76 (m, 2H), 4.93 (br, 2H), 6.14 (t, 1H), 6.91 (m, 3H), 7.28 (m, 2H), 7.60 (d, 2H), 8.22 (d, 2H)

Example 35

Carbamic acid 3-[4-(3,4-dimethoxy-phenyl)-piperazin-1-yl]-3-oxo-1-(4-trifluoromethyl-phenyl)-propyl ester; hydrochloride A title compound was prepared in the same manner as in Example 1 except for the use of ethyl-4-trifluoromethyl-benzoylacetate and 3,4-dimethoxy phenylpiperazine. The prepared title compound was dissolved in dichloromethane, and a saturated HCl/ether solution was added to the resulting mixture to obtain hydrochloride of the title compound.

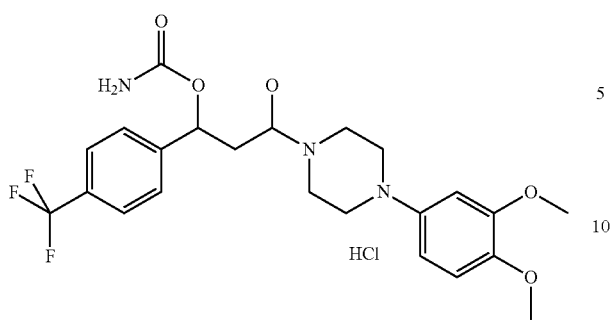

¹H NMR (200 MHz, DMSO) d: 2.90 (dd, 1H), 3.12 (dd, 1H), 3.34 (m, 4H), 3.75 (s, 3H), 3.78 (s, 3H), 3.85 (m, 4H), 6.00 (m, 1H), 6.60 (br, 2H), 7.01 (m, 2H), 7.20 (m, 1H), 7.60 (d, 2H), 7.75 (d, 2H)

Example 36

Carbamic acid 3-[4-(3,4-dimethoxy-phenyl)-piperazin-1-yl]-1-(4-nitro-phenyl)-3-oxo-propyl ester; hydrochloride A title compound was prepared in the same manner as in Example 1 except for the use of ethyl-4-nitro-benzoylacetate and 3,4-dimethoxy phenylpiperazine. The prepared title compound was dissolved in dichloromethane, and a saturated HCl/ether solution was added to the resulting mixture to obtain hydrochloride of the title compound.

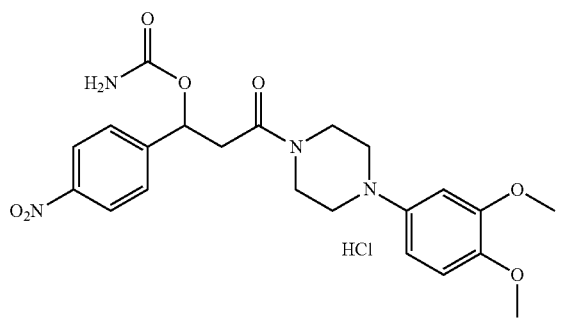 [SMILES: COc1ccc(N2CCN(C(=O)CC(OC(N)=O)c3ccc([N+](=O)[O-])cc3)CC2)cc1OC ; Cl]

¹H NMR (200 MHz, DMSO) d: 2.96 (dd, 1H), 3.16 (dd, 1H), 3.42 (m, 4H), 3.76 (s, 3H), 3.78 (s, 3H), 3.92 (m, 4H), 6.05 (m, 1H), 6.64 (br, 2H), 7.02 (m, 1H), 7.24 (m, 2H), 7.65 (d, 2H), 8.24 (d, 2H)

Example 37

Carbamic acid 3-[4-(3,4-dichloro-benzyl)-piperazin-1-yl]-3-oxo-1-phenyl-propyl ester A title compound was prepared in the same manner as in Example 1 except for the use of ethyl benzoylacetate and 3,4-dichloro benzyl piperazine.

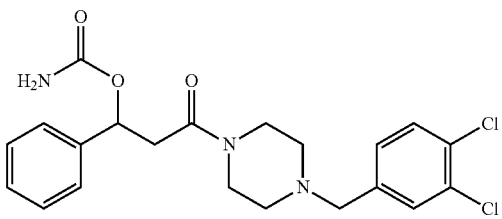 [SMILES: NC(=O)OC(CC(=O)N1CCN(Cc2ccc(Cl)c(Cl)c2)CC1)c1ccccc1]

¹H NMR (200 MHz, CDCl3) d: 2.37 (m, 4H), 2.77 (dd, 1H), 3.02 (dd, 1H), 3.45 (m, 4H), 3.63 (m, 2H), 4.74 (br, 2H), 6.11 (t, 1H), 7.16 (dd, 1H), 7.39 (m, 5H)

Example 38

Carbamic acid 3-[4-(4-chloro-phenyl)-piperazin-1-yl]-3-oxo-1-phenyl-propyl ester A title compound was prepared in the same manner as in Example 1 except for the use of ethyl benzoylacetate and 4-chloro phenylpiperazine.

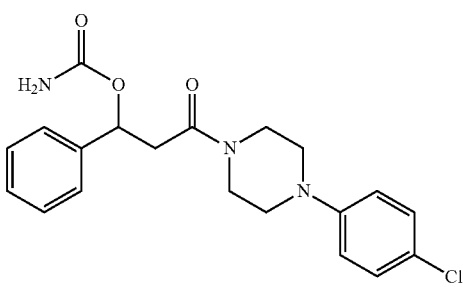 [SMILES: NC(=O)OC(CC(=O)N1CCN(c2ccc(Cl)cc2)CC1)c1ccccc1]

¹H NMR (200 MHz, CDCl3) d: 2.82 (dd, 1H), 3.07 (m, 5H), 3.58 (m, 2H), 3.74 (m, 2H), 4.81 (br, 2H), 6.13 (t, 1H), 6.84 (d, 2H), 7.38 (m, 7H)

Example 39

Carbamic acid 3-{4-[2-(3,4-dichloro-phenyl)-ethyl]-1-piperazin-1-yl}-3-oxo-1-phenyl-propyl ester A title compound was prepared in the same manner as in Example 1 except for the use of ethyl benzoylacetate and 3,4-dichloro phenethylpiperazine.

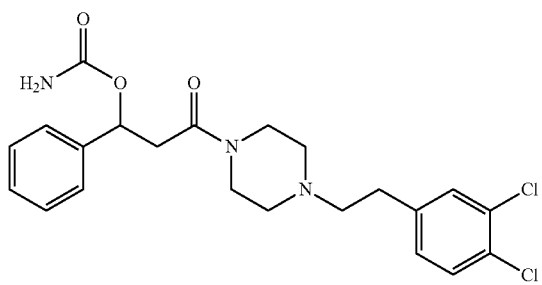 [SMILES: NC(=O)OC(CC(=O)N1CCN(CCc2ccc(Cl)c(Cl)c2)CC1)c1ccccc1]

¹H NMR (200 MHz, CDCl3) d: 2.50 (m, 6H), 2.76 (m, 3H), 3.03 (dd, 1H), 3.46 (m, 2H), 3.64 (m, 2H), 4.70 (br, 2H), 6.13 (t, 1H), 7.04 (dd, 1H), 7.38 (m, 7H)

Example 40

Carbamic acid 4-[4-(3,4-dichloro-phenyl)-piperazin-1-yl]-4-oxo-1-phenyl-butyl ester A title compound was prepared in the same manner as in Example 1 except for the use of 4-oxo-4-phenyl-butyl ester and 3,4-dichloro phenylpiperazine.

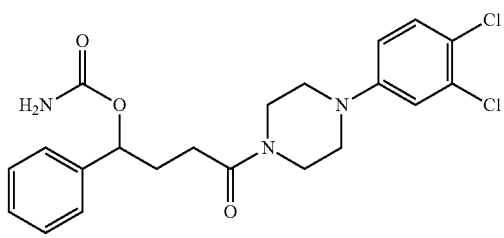 [SMILES: NC(=O)OC(CCC(=O)N1CCN(c2ccc(Cl)c(Cl)c2)CC1)c1ccccc1]

$^1$H NMR (200 MHz, CDCl3) d: 2.26 (m, 2H), 2.40 (m, 2H), 3.14 (m, 4H), 3.57 (m, 2H), 3.75 (m, 2H), 4.72 (br, 2H), 5.76 (t, 1H), 6.75 (dd, 1H), 6.96 (d, 1H), 7.37 (m, 6H)

Example 41

Carbamic acid 4-[4-(3,4-dimethoxy-phenyl)-piperazin-1-yl]-4-oxo-1-phenyl-butyl ester A title compound was prepared in the same manner as in Example 1 except for the use of 4-oxo-4-phenyl-butyl ester and 3,4-dimethoxyphenylpiperazine.

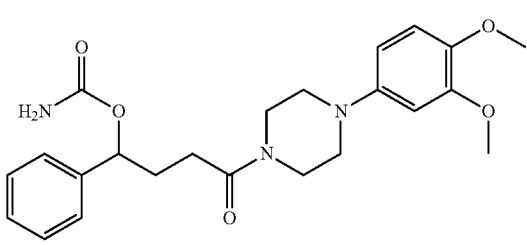 [SMILES: COc1ccc(N2CCN(C(=O)CCC(OC(N)=O)c3ccccc3)CC2)cc1OC]

$^1$H NMR (200 MHz, CDCl3) d: 2.22 (m, 2H), 2.38 (m, 2H), 3.03 (m, 4H), 3.58 (m, 2H), 3.77 (m, 2H), 3.85 (s, 3H), 3.88 (s, 3H), 4.91 (br, 2H), 5.76 (t, 1H), 6.42 (dd, 1H), 6.58 (d, 1H), 6.80 (d, 1H), 7.35 (m, 5H)

Example 42

Carbamic acid 1-(2-nitro-phenyl)-3-oxo-3-(4-phenylpiperazin-1-yl)-propyl ester

A title compound was prepared in the same manner as in Example 1 except for the use of ethyl-2-nitro-benzoylacetate and phenylpiperazine.

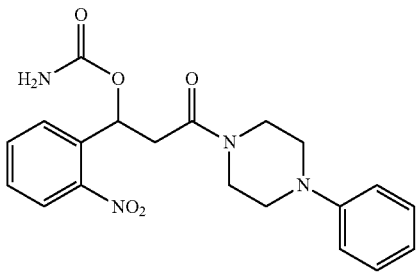 [SMILES: NC(=O)OC(CC(=O)N1CCN(c2ccccc2)CC1)c1ccccc1[N+](=O)[O-]]

$^1$H NMR (200 MHz, CDCl3) d: 2.94-3.19 (m, 6H), 3.67 (m, 4H), 4.84 (br, 2H), 6.57 (dd, 1H), 6.91 (m, 3H), 7.28 (m, 2H), 7.69 (m, 2H), 7.96 (d, 1H)

Example 43

Carbamic acid 1-(2-chloro-phenyl)-3-oxo-3-(4-phenylpiperazin-1-yl)-propyl ester

A title compound was prepared in the same manner as in Example 1 except for the use of ethyl-2-chloro-benzoylacetate and phenylpiperazine.

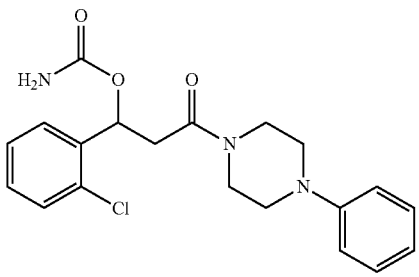 [SMILES: NC(=O)OC(CC(=O)N1CCN(c2ccccc2)CC1)c1ccccc1Cl]

$^1$H NMR (200 MHz, CDCl3) d: 2.93 (d, 2H), 3.63 (m, 4H), 3.84 (m, 4H), 4.78 (br, 2H), 6.43 (t, 1H), 6.88 (m, 3H), 7.30 (m, 5H), 7.49 (d, 1H)

Example 44

Carbamic acid 1-(2-methoxy-phenyl)-3-oxo-3-(4-phenylpiperazin-1-yl)-propyl ester A title compound was prepared in the same manner as in Example 1 except for the use of ethyl-2-methoxy-ethyl benzoylacetate and phenylpiperazine.

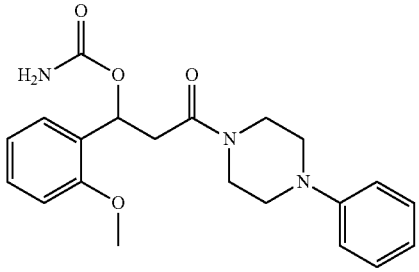 [SMILES: COc1ccccc1C(CC(=O)N1CCN(c2ccccc2)CC1)OC(N)=O]

$^1$H NMR (200 MHz, CDCl3) d: 2.90 (m, 2H), 3.15 (m, 4H), 3.73 (m, 4H), 3.86 (s, 3H), 4.76 (br, 2H), 6.40 (q, 1H), 6.93 (m, 4H), 7.27 (m, 4H), 7.39 (d, 1H)

Example 45

Carbamic acid 1-(3-trifluoromethyl-phenyl)-3-oxo-3-(4-phenylpiperazin-1-yl)-propyl ester A title compound was prepared in the same manner as in Example 1 except for the use of ethyl-3-trifluoromethyl-benzoylacetate and phenylpiperazine.

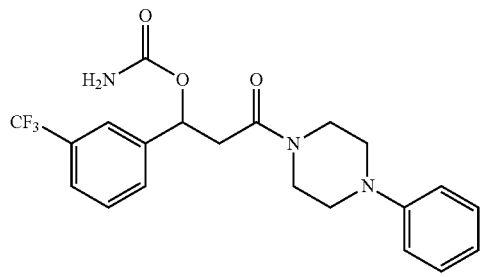 [SMILES: NC(=O)OC(CC(=O)N1CCN(c2ccccc2)CC1)c1cccc(C(F)(F)F)c1]

$^1$H NMR (200 MHz, CDCl3) d: 2.77 (m, 1H), 3.12 (m, 5H), 3.76 (m, 4H), 4.74 (br, 2H), 6.19 (q, 1H), 6.91 (m, 3H), 7.28 (m, 2H), 7.60 (m, 4H)

Example 46

Carbamic acid 1-(3-bromo-phenyl)-3-oxo-3-(4-phenylpiperazin-1-yl)-propyl ester

A title compound was prepared in the same manner as in Example 1 except for the use of ethyl-3-bromo-benzoylacetate and phenylpiperazine.

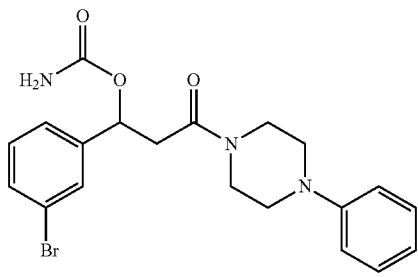 [SMILES: NC(=O)OC(CC(=O)N1CCN(c2ccccc2)CC1)c1cccc(Br)c1]

$^1$H NMR (200 MHz, CDCl3) d: 2.76 (m, 1H), 3.14 (m, 5H), 3.66 (m, 4H), 4.72 (br, 2H), 6.10 (q, 1H), 6.90 (m, 3H), 7.32 (m, 5H), 7.54 (s, 1H)

Example 47

Carbamic acid 2,2-difluoro-3-oxo-1-phenyl-3-(4-phenylpiperazin-1-yl)-propyl ester A title compound was prepared in the same manner as in Example 1 except for the use of 3-carbamoyloxy-2,2-difluoro-3-phenyl-propionic ester and phenyl piperazine.

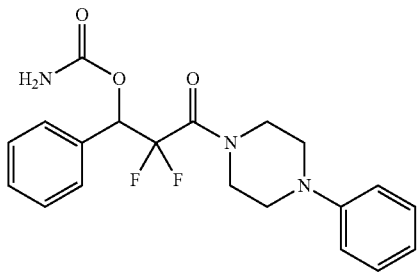 [SMILES: NC(=O)OC(c1ccccc1)C(F)(F)C(=O)N1CCN(c2ccccc2)CC1]

$^1$H NMR (200 MHz, CDCl3) d: 3.14 (m, 4H), 3.79 (d, 4H), 4.81 (br, 2H), 6.35 (q, 1H), 6.91 (m, 3H), 7.26 (m, 7H)

Example 48

Carbamic acid 1-(3,4-dimethoxy-phenyl)-3-oxo-3-(4-phenylpiperazin-1-yl)-propyl ester A title compound was prepared in the same manner as in Example 1 except for the use of ethyl-3,4-dimethoxy-benzoylacetate and phenylpiperazine.

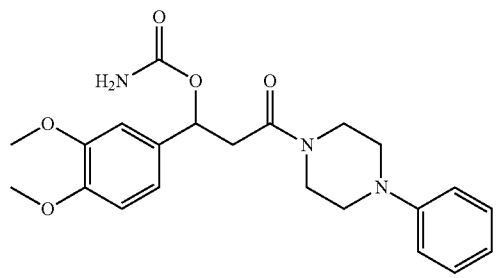 [SMILES: COc1ccc(C(CC(=O)N2CCN(c3ccccc3)CC2)OC(N)=O)cc1OC]

$^1$H NMR (200 MHz, CDCl3) d: 2.78 (dd, 1H), 3.08 (m, 5H), 3.61 (m, 4H), 3.84 (s, 3H), 3.89 (s, 3H), 4.70 (br, 2H), 6.06 (t, 1H), 6.88 (m, 5H), 7.26 (m, 3H)

Example 49

Carbamic acid-1-furan-3-yl-3-oxo-3-(4-phenyl-piperazin-1-yl)-propyl ester

A title compound was prepared in the same manner as in Example 1 except for the use of 3-furan-3-yl-3-oxo-propionic acid ethyl ester and phenylpiperazine.

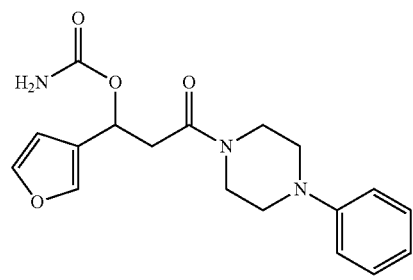 [SMILES: NC(=O)OC(CC(=O)N1CCN(c2ccccc2)CC1)c1ccoc1]

$^1$H NMR (200 MHz, CDCl3) d: 2.80 (dd, 1H), 3.09 (m, 5H), 3.71 (m, 4H), 4.67 (br, 2H), 6.15 (t, 1H), 6.4 (s, 1H), 6.93 (d, 3H), 7.38 (m, 4H)

Example 50

Carbamic acid 1-(3-methyl-phenyl)-3-oxo-3-(4-phenyl-piperazin-1-yl)-propyl ester A title compound was prepared in the same manner as in Example 1 except for the use of ethyl-3-methyl-benzoylacetate and phenylpiperazine.

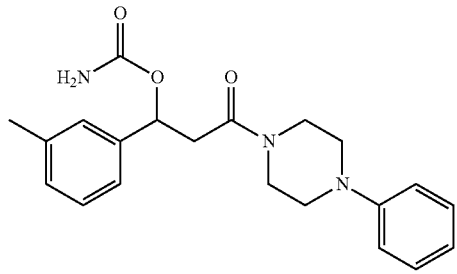 [SMILES: Cc1cccc(C(CC(=O)N2CCN(c3ccccc3)CC2)OC(N)=O)c1]

$^1$H NMR (200 MHz, CDCl3) d: 2.34 (s, 3H), 2.79 (d, 1H), 3.08 (m, 5H), 3.66 (m, 4H), 4.68 (br, 2H), 6.08 (t, 1H), 6.89 (m, 3H), 7.10 (m, 1H), 7.23 (m, 5H)

Example 51

Carbamic acid 1-(3-chloro-phenyl)-3-oxo-3-(4-phenyl-piperazin-1-yl)-propyl ester A title compound was prepared in the same manner as in Example 1 except for the use of ethyl-3-chloro-benzoylacetate and phenylpiperazine.

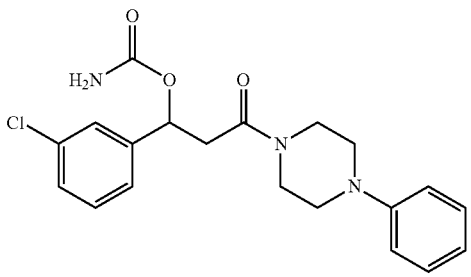 [SMILES: NC(=O)OC(CC(=O)N1CCN(c2ccccc2)CC1)c1cccc(Cl)c1]

$^1$H NMR (200 MHz, CDCl3) d: 2.77 (dd, 1H), 3.07 (m, 5H), 3.58 (m, 2H), 3.75 (m, 2H), 4.68 (br, 2H), 6.11 (q, 1H), 6.91 (m, 3H), 7.28 (m, 6H)

Example 52

Carbamic acid-2-(4-phenyl-piperazine-1-carbonyl)-1,2,3,4-tetrahydro-naphthalene-1-yl ester A title compound was prepared in the same manner as in Example 1 except for the use of 1-oxo-1,2,3,4-tetrahydro-naphthalene-2-carboxylic acid ethyl ester and phenyl piperazine.

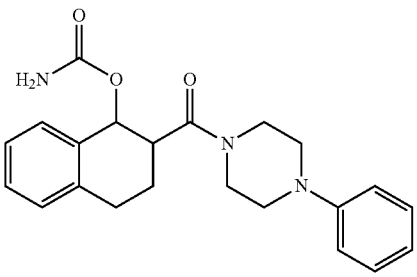 [SMILES: NC(=O)OC1c2ccccc2CCC1C(=O)N1CCN(c2ccccc2)CC1]

$^1$H NMR (200 MHz, CDCl3) d: 1.99 (d, 1H), 2.35 (q, 1H), 0.80 (m, 1H), 3.08 (m, 4H), 3.40 (m, 1H), 3.71 (m, 4H), 4.66 (br, 2H), 6.15 (s, 1H), 6.92 (m, 3H), 7.25 (m, 4H), 7.41 (d, 1H)

Example 53

Carbamic acid 1-(3,4-dichloro-phenyl)-3-oxo-3-(4-phenyl-piperazin-1-yl)-propyl ester A title compound was prepared in the same manner as in Example 1 except for the use of ethyl-3,4-dichloro-benzoylacetate and phenylpiperazine.

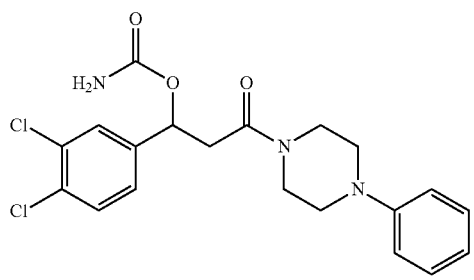 [SMILES: NC(=O)OC(CC(=O)N1CCN(c2ccccc2)CC1)c1ccc(Cl)c(Cl)c1]

$^1$H NMR (200 MHz, CDCl3) d: 2.75 (dd, 1H), 3.05 (m, 5H), 3.66 (m, 4H), 4.73 (br, 2H), 6.08 (t, 1H), 6.91 (m, 3H), 7.27 (m, 3H), 7.42 (m, 1H), 7.49 (m, 1H)

Example 54

Carbamic acid 1-(2,3,4,5,6-pentafluoro-phenyl)-3-oxo-3-(4-phenyl-piperazin-1-yl)-propyl ester A title compound was prepared in the same manner as in Example 1 except for the use of ethyl-2,3,4,5,6-pentafluoro-benzoylacetate and phenylpiperazine.

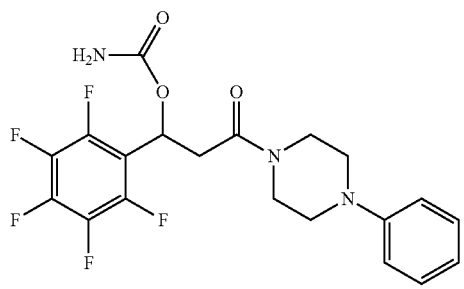 [SMILES: NC(=O)OC(CC(=O)N1CCN(c2ccccc2)CC1)c1c(F)c(F)c(F)c(F)c1F]

$^1$H NMR (200 MHz, CDCl3) d: 3.14 (m, 6H), 3.67 (m, 4H), 5.16 (br, 2H), 6.37 (t, 1H), 6.92 (m, 3H), 7.26 (m, 2H)

Example 55

Carbamic acid 1-(3,5-trifluoromethyl-phenyl)-3-oxo-3-(4-phenyl-piperazin-1-yl)-propyl ester A title compound was prepared in the same manner as in Example 1 except for the use of ethyl-3,5-trifluoromethyl-benzoylacetate and phenylpiperazine.

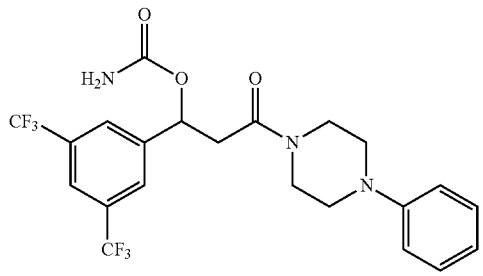

$^1$H NMR (200 MHz, CDCl3) d: 2.79 (dd, 1H), 3.12 (m, 5H), 3.67 (m, 4H), 4.71 (br, 2H), 6.27 (t, 1H), 6.92 (m, 3H), 7.28 (m, 3H), 7.84 (m, 2H)

Example 56

Carbamic acid 1-(2,4-dichloro-phenyl)-3-oxo-3-(4-phenyl-piperazin-1-yl)-propyl ester A title compound was prepared in the same manner as in Example 1 except for the use of ethyl-2,4-dichloro-benzoylacetate and phenylpiperazine.

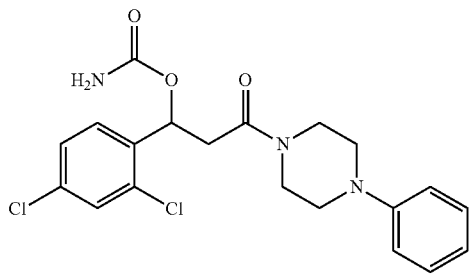 [SMILES: NC(=O)OC(CC(=O)N1CCN(c2ccccc2)CC1)c1ccc(Cl)cc1Cl]

$^1$H NMR (200 MHz, CDCl3) d: 2.91 (m, 2H), 3.17 (m, 4H), 3.74 (m, 4H), 4.76 (br, 2H), 6.38 (q, 1H), 6.92 (m, 3H), 7.31 (m, 3H), 7.44 (m, 2H)

Example 57

Carbamic acid 1-(2,5-difluoro-phenyl)-3-oxo-3-(4-phenyl-piperazin-1-yl)-propyl ester A title compound was prepared in the same manner as in Example 1 except for the use of ethyl-2,5-difluoro-benzoylacetate and phenylpiperazine.

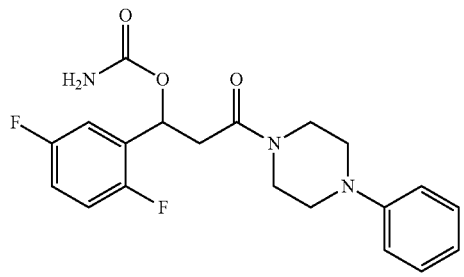 [SMILES: NC(=O)OC(CC(=O)N1CCN(c2ccccc2)CC1)c1cc(F)ccc1F]

$^1$H NMR (200 MHz, CDCl3) d: 2.87 (dd, 1H), 3.03 (q, 1H), 3.16 (m, 4H), 3.71 (m, 4H), 4.72 (br, 2H), 6.30 (q, 1H), 6.97 (m, 4H), 7.14 (m, 1H), 7.28 (m, 3H)

Example 58

Carbamic acid 1-(2,4-dimethyl-phenyl)-3-oxo-3-(4-phenyl-piperazin-1-yl)-propyl ester A title compound was prepared in the same manner as in Example 1 except for the use of ethyl-2,4-dimethyl-benzoylacetate and phenylpiperazine.

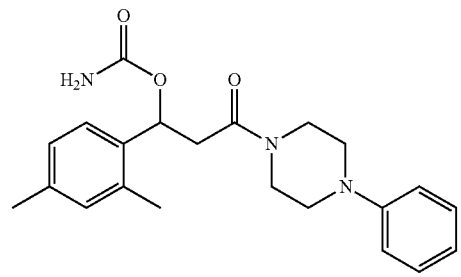 [SMILES: Cc1ccc(C(CC(=O)N2CCN(c3ccccc3)CC2)OC(N)=O)c(C)c1]

$^1$H NMR (200 MHz, CDCl3) d: 2.27 (s, 3H), 2.41 (s, 3H), 2.78 (dd, 1H), 3.05 (m, 5H), 3.68 (m, 4H), 4.74 (br, 2H), 6.28 (t, 1H), 6.95 (m, 5H), 7.26 (m, 3H)

Example 59

Carbamic acid 1-(3,4-methylenedioxy-phenyl)-3-oxo-3-(4-phenyl-piperazin-1-yl)-propyl ester A title compound was prepared in the same manner as in Example 1 except for the use of ethyl-3,4-methylenedioxy-benzoylacetate and phenylpiperazine.

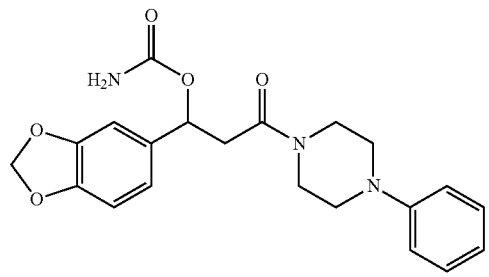 [SMILES: NC(=O)OC(CC(=O)N1CCN(c2ccccc2)CC1)c1ccc2c(c1)OCO2]

$^1$H NMR (200 MHz, CDCl3) d: 2.77 (dd, 1H), 3.09 (m, 5H), 3.67 (m, 4H), 4.65 (br, 2H), 5.96 (s, 2H), 6.05 (t, 1H), 6.77 (m, 1H), 6.89 (m, 5H), 7.28 (m, 2H)

Example 60

Carbamic acid 1-(3,4-difluoro-phenyl)-3-oxo-3-(4-phenyl-piperazin-1-yl)-propyl ester A title compound was prepared in the same manner as in Example 1 except for the use of ethyl-3,4-difluoro-benzoylacetate and phenylpiperazine.

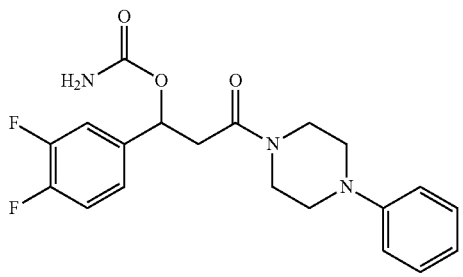 [SMILES: NC(=O)OC(CC(=O)N1CCN(c2ccccc2)CC1)c1ccc(F)c(F)c1]

$^1$H NMR (200 MHz, CDCl3) d: 2.75 (dd, 1H), 3.06 (m, 5H), 3.66 (m, 4H), 4.73 (br, 2H), 6.08 (t, 1H), 6.91 (m, 3H), 7.20 (m, 5H)

Example 61

(R)-carbamic acid 3-[4-(4-chloro-phenyl)-piperazin-1-yl]-3-oxo-1-phenyl-propyl ester (R)-3-hydroxy-3-phenylpropionic acid (1.0 g, 6.0 mmole) and 4-chloro phenylpiperazine (1.18 g, 6.0 mmole) were dissolved in 50 mL of solvent 'tetrahydrofuran at a room temperature, and EDC (1.24 g, 6.0 mmole) and HOBt (0.81 g, 6 mmole) were added dropwise to the mixture. Then, the resulting mixture was stirred at 25° C. for 5 hours. The mixture was distilled under a reduced pressure to remove excessive solvents, and the solvent-free mixture was neutralized with 1 normal aqueous sodium chloride solution (20 mL), and 25 mL of ethyl acetate was added to the resulting mixture to separate an organic phase. Then, the prepared organic phase was further extracted twice with 15 mL of ethyl acetate. The organic phase was dried over anhydrous magnesium sulfate (2 g), and filtered, and the resulting filtrate was concentrated under a reduced pressure, and separated and purified with column chromatography (hexane:ethyl acetate=1:1 to 1:10). The resulting reaction product (0.345 g, 1 mmol) was dissolved in tetrahydrofuran (15 mL), and 1,1'-carbodiimidazole (0.325 g, 2 mmol) was then added to the reaction product, and the resulting reaction mixture was stirred at a room temperature for 1 hour. Then, excessive aqueous ammonium hydroxide was added to the reaction mixture, and resulting reaction mixture was stirred at a room temperature for additional 2 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1 to ethyl acetate) to obtain a title compound.

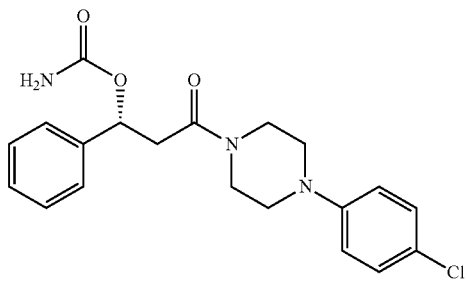 [SMILES: NC(=O)O[C@H](CC(=O)N1CCN(c2ccc(Cl)cc2)CC1)c1ccccc1]

$^1$H NMR (200 MHz, CDCl3) d: 2.82 (dd, 1H), 3.07 (m, 5H), 3.58 (m, 2H), 3.74 (m, 2H), 4.81 (br, 2H), 6.13 (t, 1H), 6.84 (d, 2H), 7.38 (m, 7H)

Title compounds of Examples 62 to 71 and 78 to 87 were prepared in the same manner as in Example 61, except that the different starting materials were used in the Examples 62 to 71 and 78 to 87.

Example 62

(R)-carbamic acid 3-[4-(4-fluoro-phenyl)-piperazin-1-yl]-3-oxo-1-phenyl-propyl ester A title compound was synthesized in the same manner as in Example 61 except for the use of (R)-3-hydroxy-3-phenyl-propionic acid and 4-fluoro phenylpiperazine.

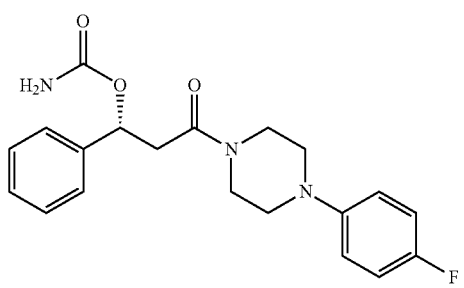

$^1$H NMR (200 MHz, CDCl3) d: 2.82 (dd, 1H), 3.03 (m, 5H), 3.60 (m, 2H), 3.76 (m, 2H), 4.73 (br, 2H), 6.16 (t, 1H), 6.95 (m, 4H), 7.38 (m, 5H)

Example 63

(R)-carbamic acid 3-[4-(4-ethoxy-phenyl)-piperazin-1-yl]-3-oxo-1-phenyl-propyl ester A title compound was synthesized in the same manner as in Example 61 except for the use of (R)-3-hydroxy-3-phenyl-propionic acid and 4-ethoxy phenylpiperazine.

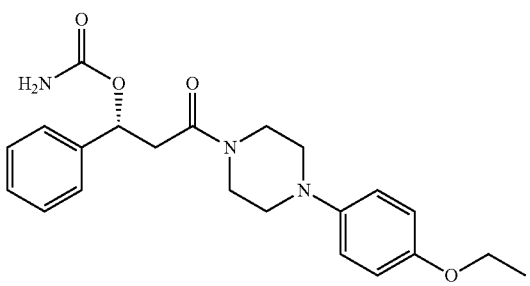 [SMILES: CCOc1ccc(N2CCN(C(=O)C[C@@H](OC(N)=O)c3ccccc3)CC2)cc1]

¹H NMR (500 MHz, CDCl3) d: 1.38 (t, 3H), 2.80 (dd, 1H), 3.00 (m, 5H), 3.55 (m, 2H), 3.74 (m, 2H), 3.99 (q, 2H), 4.81 (br, 2H), 6.12 (t, 1H), 6.84 (m, 4H), 7.33 (m, 5H)

Example 64

(S)-carbamic acid 3-[4-(3,4-difluoro-phenyl)-piperazin-1-yl]-3-oxo-1-phenyl-propyl ester A title compound was synthesized in the same manner as in Example 61 except for the use of (S)-3-hydroxy-3-phenyl-propionic acid and 3,4-difluoro phenylpiperazine.

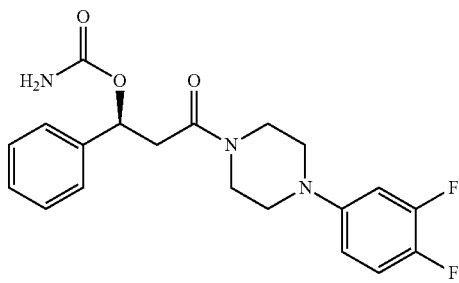 [SMILES: NC(=O)O[C@@H](CC(=O)N1CCN(c2ccc(F)c(F)c2)CC1)c1ccccc1]

¹H NMR (200 MHz, CDCl3) d: 2.82 (dd, 1H), 3.03 (m, 5H), 3.59 (m, 2H), 3.76 (m, 2H), 4.76 (br, 2H), 6.14 (t, 1H), 6.68 (m, 2H), 7.05 (q, 1H), 7.40 (m, 5H)

Example 65

(S)-carbamic acid 3-[4-(3,4-dimethoxy-phenyl)-piperazin-1-yl]-3-oxo-1-phenyl-propyl ester A title compound was synthesized in the same manner as in Example 61 except for the use of (S)-3-hydroxy-3-phenyl-propionic acid and 3,4-dimethoxy phenylpiperazine.

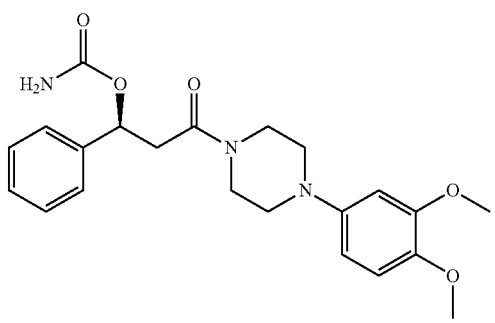 [SMILES: COc1ccc(N2CCN(C(=O)C[C@H](OC(N)=O)c3ccccc3)CC2)cc1OC]

¹H NMR (200 MHz, CDCl3) d: 2.82 (dd, 1H), 3.04 (m, 5H), 3.61 (m, 2H), 3.77 (m, 2H), 3.88 (d, 6H), 4.77 (br, 2H), 6.15 (t, 1H), 6.42 (d, 1H), 6.57 (s, 1H), 6.82 (d, 1H), 7.41 (m, 5H)

Example 66

(S)-carbamic acid 3-[4-(3,4-dichloro-phenyl)-piperazin-1-yl]-3-oxo-1-phenyl-propyl ester A title compound was synthesized in the same manner as in Example 61 except for the use of (S)-3-hydroxy-3-phenyl-propionic acid and 3,4-dichloro phenylpiperazine.

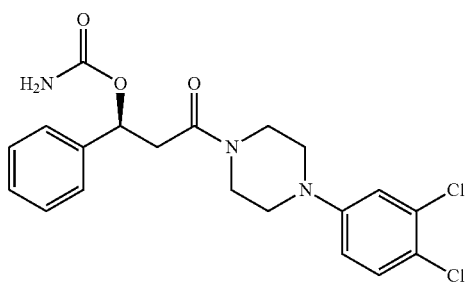 [SMILES: NC(=O)O[C@@H](CC(=O)N1CCN(c2ccc(Cl)c(Cl)c2)CC1)c1ccccc1]

¹H NMR (200 MHz, CDCl3) d: 2.82 (dd, 1H), 3.09 (m, 5H), 3.58 (m, 2H), 3.74 (m, 2H), 4.81 (br, 2H), 6.14 (t, 1H), 6.73 (dd, 1H), 6.94 (d, 1H), 7.40 (m, 6H)

Example 67

(R)-carbamic acid 3-[4-(3,4-difluoro-phenyl)-piperazin-1-yl]-3-oxo-1-phenyl-propyl ester A title compound was synthesized in the same manner as in Example 61 except for the use of (R)-3-hydroxy-3-phenyl-propionic acid and 3,4-difluoro phenylpiperazine.

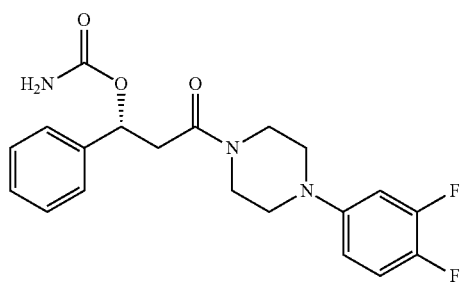

¹H NMR (200 MHz, CDCl3) d: 2.82 (dd, 1H), 3.03 (m, 5H), 3.59 (m, 2H), 3.76 (m, 2H), 4.76 (br, 2H), 6.14 (t, 1H), 6.68 (m, 2H), 7.05 (q, 1H), 7.40 (m, 5H)

Example 68

(R)-carbamic acid 3-[4-(3,4-dichloro-phenyl)-piperazin-1-yl]-3-oxo-1-phenyl-propyl ester A title compound was synthesized in the same manner as in Example 61 except for the use of (R)-3-hydroxy-3-phenyl-propionic acid and 3,4-dichloro phenylpiperazine.

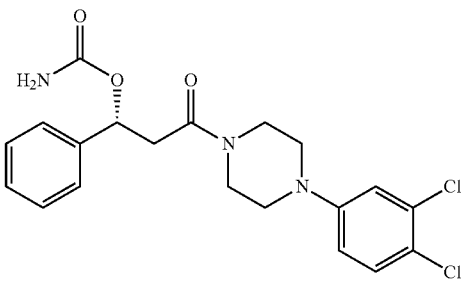

¹H NMR (200 MHz, CDCl3) d: 2.82 (dd, 1H), 3.09 (m, 5H), 3.58 (m, 2H), 3.74 (m, 2H), 4.81 (br, 2H), 6.14 (t, 1H), 6.73 (dd, 1H), 6.94 (d, 1H), 7.40 (m, 6H)

Example 69

(S)-carbamic acid 3-[4-(4-methoxy-phenyl)-piperazin-1-yl]-3-oxo-1-phenyl-propyl ester A title compound was synthesized in the same manner as in Example 61 except for the use of (S)-3-hydroxy-3-phenyl-propionic acid and 4-methoxy phenylpiperazine.

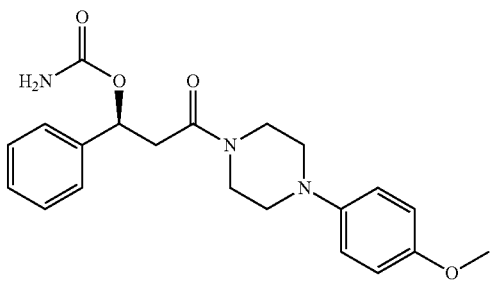 [SMILES: COc1ccc(N2CCN(C(=O)C[C@H](OC(N)=O)c3ccccc3)CC2)cc1]

¹H NMR (200 MHz, CDCl3) d: 3.00 (m, 6H), 3.60 (m, 2H), 3.79 (m, 5H), 4.82 (br, 2H), 6.18 (t, 1H), 6.88 (m, 4H), 7.38 (m, 5H)

Example 70

(R)-carbamic acid 3-[4-(4-methoxy-phenyl)-piperazin-1-yl]-3-oxo-1-phenyl-propyl ester A title compound was synthesized in the same manner as in Example 61 except for the use of (R)-3-hydroxy-3-phenyl-propionic acid and 4-methoxy phenylpiperazine.

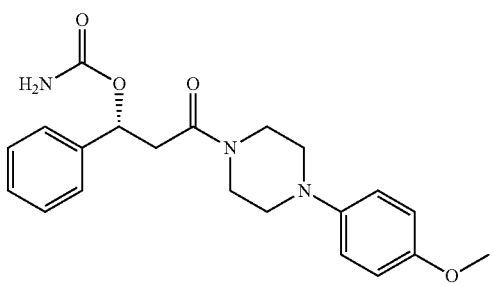 [SMILES: COc1ccc(N2CCN(C(=O)C[C@@H](OC(N)=O)c3ccccc3)CC2)cc1]

¹H NMR (200 MHz, CDCl3) d: 3.00 (m, 6H), 3.60 (m, 2H), 3.79 (m, 5H), 4.82 (br, 2H), 6.18 (t, 1H), 6.88 (m, 4H), 7.38 (m, 5H)

Example 71

(R)-carbamic acid 3-[4-(3,4-dimethoxy-phenyl)-piperazin-1-yl]-3-oxo-1-phenyl-propyl ester A title compound was synthesized in the same manner as in Example 61 except for the use of (R)-3-hydroxy-3-phenyl-propionic acid and 3,4-dimethoxy phenylpiperazine.

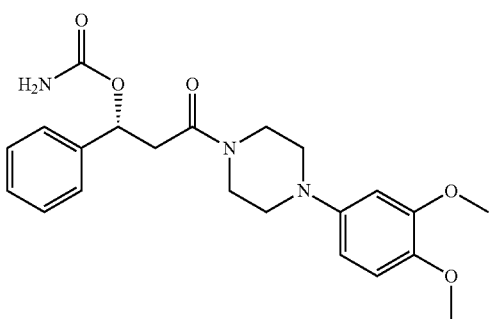 [SMILES: COc1ccc(N2CCN(C(=O)C[C@@H](OC(N)=O)c3ccccc3)CC2)cc1OC]

¹H NMR (200 MHz, CDCl3) d: 2.82 (dd, 1H), 3.04 (m, 5H), 3.61 (m, 2H), 3.77 (m, 2H), 3.88 (d, 6H), 4.77 (br, 2H), 6.15 (t, 1H)

Example 72

Phenethyl-carbamic acid-(R)-3-[4-(3,4-dimethoxy-phenyl)-piperazin-1-yl]-3-oxo-1-phenyl-propyl ester (R)-3-hydroxy-3-phenylpropionic acid (1.0 g, 6.0 mmole) and 3,4-dimethoxy phenyl piperazine (1.18 g, 6.0 mmole) were dissolved in 50 mL of a solvent 'tetrahydrofuran at a room temperature, and EDC (1.24 g, 6.0 mmole) and HOBt (0.81 g, 6 mmole) were added dropwise to the mixture. Then, the resulting mixture was stirred at 25° C. for 5 hours. The mixture was distilled under a reduced pressure to remove excessive solvents, and the solvent-free mixture was neutralized with 1 normal aqueous sodium chloride solution (20 mL), and 25 mL of ethyl acetate was added to the resulting mixture to separate an organic phase. Then, the prepared organic phase was further extracted twice with 15 mL of ethyl acetate. The organic phase was dried over anhydrous magnesium sulfate (2 g), and filtered, and the resulting filtrate was concentrated under a reduced pressure, and separated and purified with column chromatography (hexane:ethyl acetate=1:1 to 1:10). The resulting reaction product (0.345 g, 1 mmol) was dissolved in tetrahydrofuran (15 mL), and 1,1'-carbodiimidazole (0.325 g, 2 mmol) was then added to the reaction product, and the resulting reaction mixture was stirred at a room temperature for 1 hour. Then, excessive phenethylamine was added to the reaction mixture, and resulting reaction mixture was stirred at a room temperature for additional 2 hours. The reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane:ethyl acetate=1:1 to ethyl acetate) to obtain a title compound.

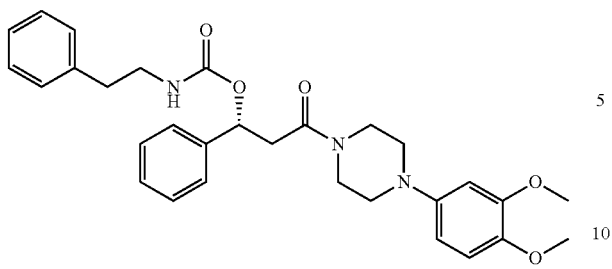

¹H NMR (200 MHz, CDCl3) d: 2.76 (m, 4H), 2.89 (m, 4H), 3.37 (m, 2H), 3.56 (m, 2H), 3.74 (m, 2H), 3.78 (s, 3H), 3.82 (s, 3H), 6.11 (t, 1H), 6.78 (d, 2H), 7.13 (m, 2H), 7.18 (m, 1H), 7.20 (m, 4H), 7.35 (m, 5H)

Example 73

Piperidine-1-carboxylic acid-(R)-3-[4-(3,4-dimethoxy-phenyl)-piperazin-1-yl]-3-oxo-1-phenyl propyl ester A title compound was synthesized in the same manner as in Example 72, except that piperidine was used instead of phenethylamine.

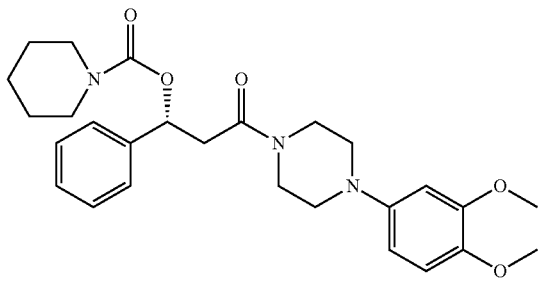 [SMILES: COc1ccc(N2CCN(C(=O)C[C@@H](OC(=O)N3CCCCC3)c3ccccc3)CC2)cc1OC]

¹H NMR (200 MHz, CDCl3) d: 2.80 (m, 1H), 2.89 (m, 1H), 2.97 (m, 3H), 3.10 (m, 1H), 3.42 (m, 4H), 3.57 (m, 1H), 3.61 (m, 1H), 3.72 (m, 2H), 3.81 (s, 3H), 3.84 (s, 3H), 610 (t, 1H), 6.41 (d, 1H), 6.53 (d, 1H), 6.77 (d, 1H), 7.32 (m, 5H)

Example 74

Butyl-carbamic acid-(R)-3-[4-(3,4-dimethoxy-phenyl)-piperazin-1-yl]-3-oxo-1-phenyl-propyl ester A title compound was synthesized in the same manner as in Example 72, except that butylamine was used instead of phenethylamine.

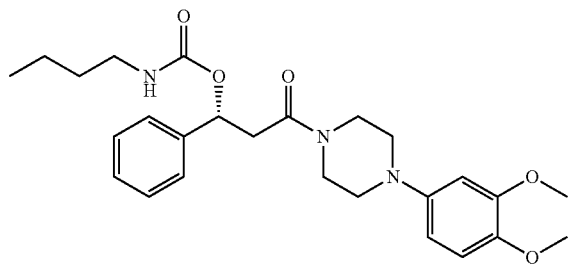 [SMILES: CCCCNC(=O)O[C@H](CC(=O)N1CCN(c2ccc(OC)c(OC)c2)CC1)c1ccccc1]

¹H NMR (200 MHz, CDCl3) d: 1.31 (m, 3H), 1.44 (m, 2H), 2.83 (m, 1H), 3.06 (m, 5H), 3.14 (m, 4H), 3.58 (m, 2H), 3.74 (m, 2H), 3.83 (s, 3H), 3.86 (s, 3H), 4.91 (t, 1H), 6.09 (m, 1H), 6.41 (d, 1H), 6.55 (d, 1H), 6.79 (d, 1H), 7.34 (m, 5H)

Example 75

4-methyl-piperazine-1-carboxylic acid-(R)-3-[4-(3,4-dimethoxy-phenyl)-piperazin-1-yl]-3-oxo-1-phenyl-propyl ester A title compound was synthesized in the same manner as in Example 72, except that 4-methylpiperazine was used instead of phenethylamine.

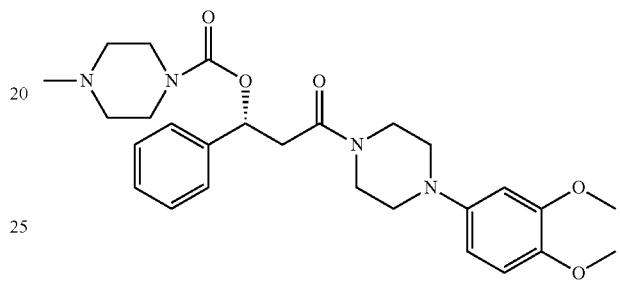

¹H NMR (200 MHz, CDCl3) d: 2.24 (m, 4H), 2.00 (s, 3H), 2.96 (m, 2H), 3.05 (m, 3H), 3.09 (m, 1H), 3.51 (m, 6H), 3.68 (m, 1H), 3.72 (m, 1H), 3.82 (s, 3H), 3.86 (s, 3H), 6.11 (t, 1H), 6.39 (d, 1H), 6.51 (d, 1H), 6.77 (d, 1H), 7.24 (d, 1H), 7.32 (m, 4H)

Example 76

(R)-carbamic acid 3-[4-(4-amino-phenyl)-piperazin-1-yl]-3-oxo-1-phenyl-propyl ester (R)-3-hydroxy-3-phenylpropionic acid (3.0 mmole) and 4-nitro phenylpiperazine (3 mmole) were dissolved in 20 mL of tetrahydrofuran at a room temperature, and EDC (6.0 mmole, 1-Ethyl-3-(3-dimethylaminopropyl)-carbodiimide) and HOBt (6 mmole, N-Hydroxybenzotriazole) were added dropwise to the mixture. Then, the resulting mixture was stirred at 25° C. for 5 hours. 20 mL of ethyl acetate was added three times to the mixture to extract an organic phase, and the prepared organic phase was dried over anhydrous magnesium sulfate (2 g), and filtered, and the resulting filtrate was concentrated under a reduced pressure, and purified with column chromatography (hexane:ethyl acetate=1:1). The resulting reaction product (1 mmol) was dissolved in methanol (20 mL), and subject to the reduction reaction at the presence of a palladium on charcoal (Pd/C) for 5 hours. The resulting reduction reaction product was concentrated under a reduced pressure to remove methanol, and extracted several times with ethyl acetate to separate an organic phase. The prepared organic phase was dried over anhydrous magnesium sulfate, and filtered, and the resulting filtrate was concentrated under a reduced pressure to obtain an intermediate reduced to an amino group (NH2). The intermediate reaction product prepared thus was dissolved in hydrofuran (10 mL), and 1,1'-carbodiimidazole (2 mmol) was added to the reaction product, and stirred at a room temperature for 1 hour. Then, excessive ammonium hydroxide was added to the resulting reaction mixture, and the reaction mixture was stirred at a room temperature for additional 2 hours. The resulting reaction mixture was diluted with water, and extracted several times with ethyl acetate to obtain an organic phase. The prepared organic phase was dried over magnesium sulfate, and concentrated under a reduced pressure. The resulting pellet was purified with column chromatography (hexane: ethyl acetate=1:1 to ethyl acetate) to obtain a title compound.

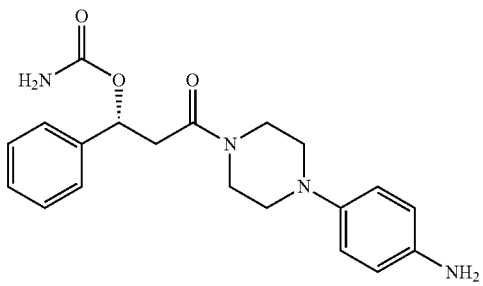 [SMILES: NC(=O)O[C@H](CC(=O)N1CCN(c2ccc(N)cc2)CC1)c1ccccc1]

$^1$H NMR (200 MHz, CDCl3) d: 2.78 (m, 1H), 2.91 (m, 2H), 3.02 (m, 2H), 3.53 (m, 3H), 3.68 (m, 2H), 5.27 (br, 2H), 6.10 (t, 1H), 6.61 (d, 1H), 6.73 (d, 1H), 6.91 (m, 1H), 7.00 (m, 1H), 7.32 (m, 6H)

Example 77

4-[2-oxo-2-(4-phenyl-piperazin-1-yl)-ethyl]-1,4-dihydro-benzo[d][1,3]oxazin-2-one Ethyl 2-nitro benzoylacetate (2.887 mmol) and phenylpiperazine (2.887 mmol) were dissolved in toluene, and refluxed for 24 hours. The resulting mixture was concentrated under a reduced pressure to obtain a crude compound. The prepared crude compound was dissolved in methanol, and cooled to 0° C., and sodium borohydride (2.887 mmol) was added slowly to the resulting mixture. The mixture was stirred at a room temperature for 2 hours, and concentrated under a reduced pressure to remove solvents. Then, the resulting mixture was diluted with water, and extracted several times with ethyl acetate to obtain an organic phase. The prepared organic phase was dried over magnesium sulfate, filtered, and then concentrated under a reduced pressure. The resulting pellet was purified with column chromatography (hexane:ethyl acetate=1:1) to obtain a compound. The prepared compound (3-(2-nitro-phenyl)-3-hydroxy-1-(4-phenyl-piperazin-1-yl)-propan-1-one, 3 mmol) was dissolved in methanol, and subject to the hydrogenation reaction at the presence of a palladium catalyst to obtain an amino compound with reduced nitro group. The prepared compound (1.21 mmol) was dissolved in tetrahydrofuran (20 mL), and tri-ethylamine (3 mmol) was added to the resulting reaction mixture. Phosgene (2.4 M toluene solution, 1.21 mmol) was added slowly to the reaction mixture. In this case, a temperature of the reaction product was maintained in a temperature range of no more than 10° C. The reaction product was stirred at a room temperature for 16 hours, diluted with ammonium hydroxide, and then extracted several times with ethyl acetate. The resulting organic phase was dried over magnesium sulfate, and filtered, and the resulting filtrate was concentrated under a reduced pressure, and re-crystallized from ethyl acetate to prepare a final compound.

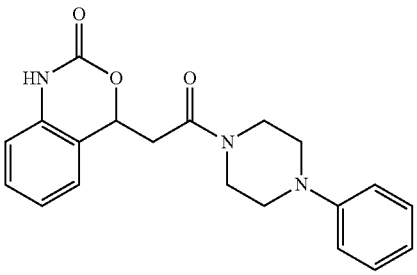 [SMILES: O=C1Nc2ccccc2C(CC(=O)N2CCN(c3ccccc3)CC2)O1]

$^1$H NMR (200 MHz, CDCl3) d: 3.07 (m, 6H), 3.54 (m, 2H), 3.78 (m, 2H), 6.01 (t, 1H), 6.88 (m, 4H), 7.05 (m, 1H), 7.26 (m, 4H), 8.46 (s, 1H)

Example 78

(R)-carbamic acid 3-[4-(3-hydroxy-4-methoxy)-phenyl piperazin-1-yl]-1-phenyl-propyl ester A title compound was synthesized in the same manner as in Example 61 except for the use of (R)-3-hydroxy-3-phenyl-propionic acid and 4-methoxy-3-hydroxy phenylpiperazine.

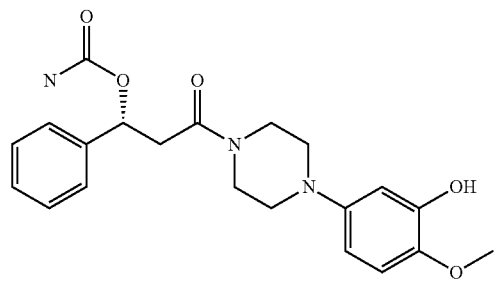 [SMILES: COc1ccc(N2CCN(C(=O)C[C@@H](OC(N)=O)c3ccccc3)CC2)cc1O]

$^1$H NMR (200 MHz, CDCl3) d: 3.01 (m, 8H), 3.50 (m, 2H), 3.72 (m, 2H), 3.84 (s, 3H), 4.77 (Br, 2H), 5.92 (s, 1H), 6.18 (t, 1H), 6.41 (dd, 1H), 6.60 (d, 1H), 6.84 (d, 1H), 7.39 (m, 5H)

Example 79

(S)-carbamic acid 3-[4-(4-fluoro)-phenyl piperazin-1-yl]-3-oxo-1-phenyl-propyl ester A title compound was synthesized in the same manner as in Example 61 except for the use of (S)-3-hydroxy-3-phenyl-propionic acid and 4-fluoro phenylpiperazine.

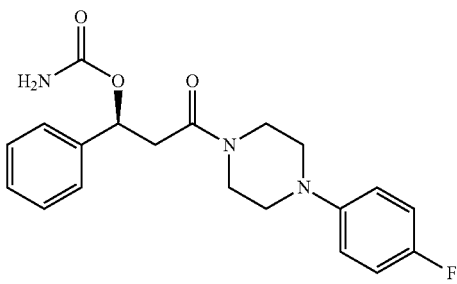 [SMILES: NC(=O)O[C@@H](CC(=O)N1CCN(c2ccc(F)cc2)CC1)c1ccccc1]

$^1$H NMR (200 MHz, CDCl3) d: 2.82 (dd, 1H), 3.03 (m, 5H), 3.60 (m, 2H), 3.76 (m, 2H), 4.73 (br, 2H), 6.16 (t, 1H), 6.95 (m, 4H), 7.38 (m, 5H

Example 80

(R)-carbamic acid 3-[4-(4-methyl)-phenyl piperazin-1-yl]-3-oxo-1-phenyl-propyl ester A title compound was synthesized in the same manner as in Example 61 except for the use of (R)-3-hydroxy-3-phenyl-propionic acid and 4-methylphenylpiperazine.

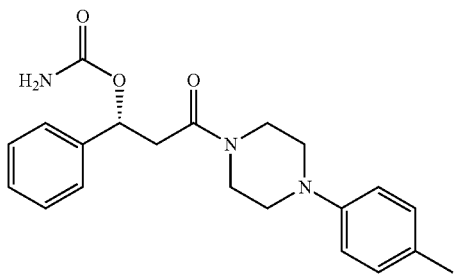 [SMILES: Cc1ccc(N2CCN(C(=O)C[C@@H](OC(N)=O)c3ccccc3)CC2)cc1]

$^1$H NMR (200 MHz, CDCl3) d: 2.30 (s, 3H), 2.82 (dd, 1H), 3.05 (m, 5H), 3.60 (m, 2H), 3.77 (m, 2H), 4.77 (br, 2H), 6.15 (t, 1H), 6.84 (d, 2H), 7.10 (d, 2H), 7.38 (m, 5H)

Example 81

(S)-carbamic acid 3-[4-(4-methyl)-phenyl piperazin-1-yl]-3-oxo-1-phenyl-propyl ester A title compound was synthesized in the same manner as in Example 61 except for the use of (S)-3-hydroxy-3-phenyl-propionic acid and 4-methylphenylpiperazine.

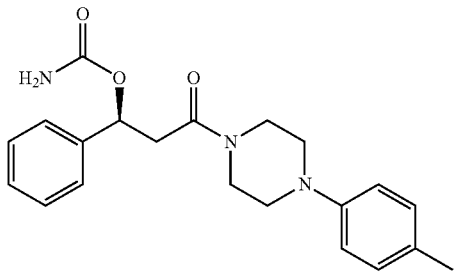 [SMILES: Cc1ccc(N2CCN(C(=O)C[C@H](OC(N)=O)c3ccccc3)CC2)cc1]

$^1$H NMR (200 MHz, CDCl3) d: 2.30 (s, 3H), 2.82 (dd, 1H), 3.05 (m, 5H), 3.60 (m, 2H), 3.77 (m, 2H), 4.77 (br, 2H), 6.15 (t, 1H), 6.84 (d, 2H), 7.10 (d, 2H), 7.38 (m, 5H)

Example 82

(R)-carbamic acid 3-[4-(2,4-difluoro)-phenyl piperazin-1-yl]-3-oxo-1-phenyl-propyl ester A title compound was synthesized in the same manner as in Example 61 except for the use of (R)-3-hydroxy-3-phenyl-propionic acid and 2,4-difluorophenylpiperazine.

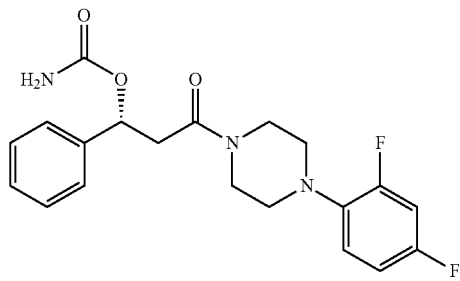

$^1$H NMR (200 MHz, CDCl3) d: 2.95 (m, 6H), 3.61 (m, 2H), 3.80 (m, 2H), 4.69 (br, 2H), 6.15 (t, 1H), 6.82 (m, 3H), 7.35 (m, 5H)

Example 83

(R)-carbamic acid 3-[4-(4-hydroxyl-phenyl piperazin-1-yl]-3-oxo-1-phenyl-propyl ester A title compound was synthesized in the same manner as in Example 61 except for the use of (R)-3-hydroxy-3-phenyl-propionic acid and 4-hydroxyphenylpiperazine.

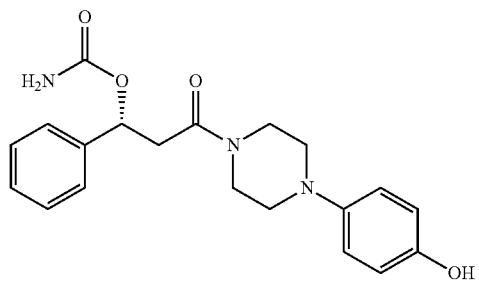 [SMILES: NC(=O)O[C@H](CC(=O)N1CCN(c2ccc(O)cc2)CC1)c1ccccc1]

$^1$H NMR (200 MHz, DMSO) d: 2.82 (m, 6H), 3.56 (m, 4H), 5.93 (t, 1H), 6.51 (br, 2H), 6.67 (d, 2H), 6.78 (d, 2H), 7.37 (m, 5H), 8.88 (s, 1H)

Example 84

(S)-carbamic acid 3-[4-(4-hydroxy)-phenyl piperazin-1-yl]-3-oxo-1-phenyl-propyl ester A title compound was synthesized in the same manner as in Example 61 except for the use of (S)-3-hydroxy-3-phenyl-propionic acid and 4-hydroxyphenylpiperazine.

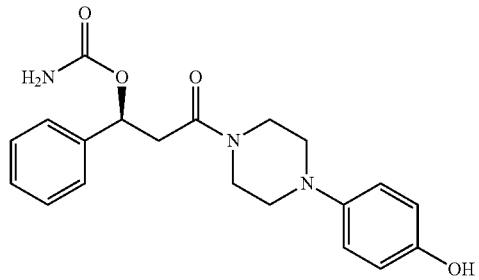 [SMILES: NC(=O)O[C@@H](CC(=O)N1CCN(c2ccc(O)cc2)CC1)c1ccccc1]

¹H NMR (200 MHz, DMSO) d: 2.82 (m, 6H), 3.56 (m, 4H), 5.93 (t, 1H), 6.51 (br, 2H), 6.67 (d, 2H), 6.78 (d, 2H), 7.37 (m, 5H), 8.88 (s, 1H)

Example 85

(S)-carbamic acid 3-[4 (4-chloro)-phenyl piperazin-1-yl]-3-oxo-1-phenyl-propyl ester A title compound was synthesized in the same manner as in Example 61 except for the use of (S)-3-hydroxy-3-phenyl-propionic acid and 4-chlorophenylpiperazine.

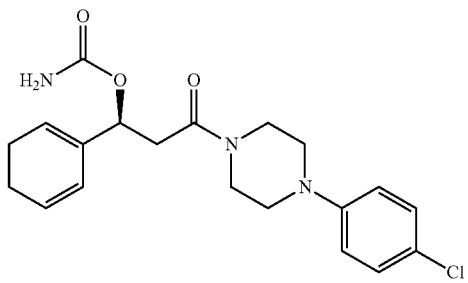 [SMILES: NC(=O)O[C@@H](CC(=O)N1CCN(c2ccc(Cl)cc2)CC1)C1=CCCC=C1]

¹H NMR (200 MHz, CDCl3) d: 2.82 (dd, 1H), 3.07 (m, 5H), 3.58 (m, 2H), 3.74 (m, 2H), 4.81 (br, 2H), 6.13 (t, 1H), 6.84 (d, 2H), 7.38 (m, 7H)

Example 86

Carbamic acid (R)-3-[4-(3-hydroxy-4-methoxy-phenyl)-piperazin-1-yl]-3-oxo-1-phenyl-propyl ester A title compound was synthesized in the same manner as in Example 61 except for the use of (R)-3-hydroxy-3-phenyl-propionic acid and 3-methoxy-4-hydroxyphenylpiperazine.

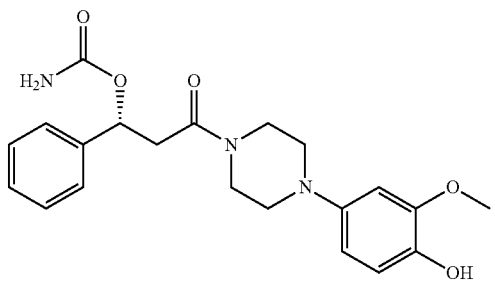 [SMILES: COc1cc(N2CCN(C(=O)C[C@@H](OC(N)=O)c3ccccc3)CC2)ccc1O]

¹H NMR (200 MHz, CDCl3) d: 2.98 (m. 8H), 3.51 (m, 1H), 3.82 (m, 1H), 3.88 (s, 3H), 4.81 (br, 2H), 5.40 (s, 1H), 6.01 (t, 1H), 6.4 (dd, 1H), 6.92 (d, 1H), 7.39 (m, 5H)

Example 87

Carbamic acid (R)-3-[4-(3-methoxy-4-hydroxy-phenyl)-piperazin-1-yl]-3-oxo-1-phenyl-propyl ester A title compound was synthesized in the same manner as in Example 61 except for the use of (R)-3-hydroxy-3-phenyl-propionic acid and 3-hydroxy-4-methoxyphenylpiperazine.

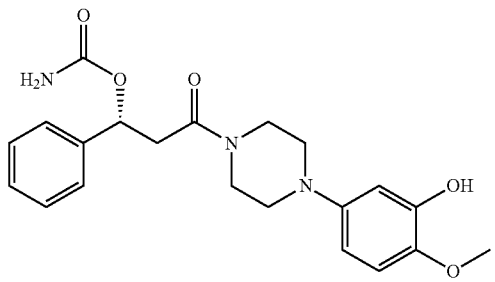 [SMILES: COc1ccc(N2CCN(C(=O)C[C@@H](OC(N)=O)c3ccccc3)CC2)cc1O]

¹H NMR (200 MHz, CDCl3) d: 2.99 (m. 8H), 3.47 (m, 1H), 3.50 (m, 1H), 3.84 (s, 3H), 4.77 (br, 2H), 6.20 (t, 1H), 6.45 (dd, 1H), 6.59 (d, 1H), 6.80 (d, 1H), 7.37 (m, 5H)

The compounds as listed above were tested for analgesic effects using the following animal models 2. Acetic Acid-Induced Writhing Test in Mouse An acetic acid-induced writhing test is one of models for measuring an analgesic effect of drugs. A test material dissolved in a suitable vehicle was orally administered to a male ICR mouse weighing 30 to 35 g at an amount of 10 mg/kg. After 1 hour of the oral administration, 10 mg/ml of an aqueous 0.8% acetic acid solution was intraperitoneally injected into the male ICR mouse to induce the abdominal pain of the male ICR mouse. Right after the administration of acetic acid, the male ICR mouse was put into an empty cage, and the number of writhing behaviors of the mice was counted for 10 minutes. The term "writhing represents a reflex action in which the mouse overtly extends its abdomen by stretching its hind legs due to the abdominal pain. The analgesic effect of the test material is represented by the 'suppression of pain response'{[(Writhing number of vehicle-administered group−Writhing number of Test material-administered group)/(Writhing number of Solvent-administered group)]×100%}. From these results, it was observed that the higher analgesic effect shows the higher suppression of pain response.

3. Hot Plate Test in Mouse

A hot plate test is one of representative models for measuring an analgesic effect of drugs. A test material dissolved in a suitable vehicle was orally administered to a male ICR mouse weighing 25 to 30 g at an amount of 30 mg/kg. After 1 hour of the oral administration, the mouse was put on a hot plate (55° C.). A latency was recorded from the time right after a mouse is put on a hot plate to the time when avoidance responses (flinching, licking, jumping, etc.) to pain are observed from forefeet or rear legs of the mouse. The analgesic effect of the test material is represented by the 'Increase in latency of avoidance response' {[(Latency of avoidance response to pain of Test material-administered group−Latency of avoidance response to pain of vehicle-administered group)/(Latency of avoidance response to pain of Solvent-administered group)]×100%}. From these results, it was observed that the higher analgesic effect shows the higher increase in latency of avoidance response.

TABLE 1

Results on acetic acid - induced writhing test and hot plate test) in mouse

| Compound | Writhing Test Suppression of pain response (10 mg/kg, p.o) | Hot Plate Test Increase in latency of avoidance response (30 mg/kg, p.o) |
|---|---|---|
| Example 1: carbamic acid 3-[4-(4-fluoro-phenyl)-piperazin-1-yl]-3-oxo-1-phenyl-propyl ester | 73.5% | 17.0% |
| Example 2: carbamic acid 3-[4-(4-methoxy-phenyl)-piperazin-1-yl]-3-oxo-1-phenyl-propyl ester | 54.6% | 37.5% |
| Example 3: carbamic acid 3-[4-(3,4-dichloro-phenyl)-piperazin-1-yl]-3-oxo-1-phenyl-propyl ester | 65.0% | 38.5% |
| Example 4: carbamic acid 3-oxo-1-phenyl-3-(4-p-tolyl-piperazin-1-yl)-propyl ester | 74.6% | 34.1% |
| Example 5: carbamic acid 3-[4-(3,4-dimethoxy-phenyl)-piperazin-1-yl]-3-oxo-1-phenyl-propyl ester | 79.7% | 39.2% |
| Example 6: carbamic acid 1-(4-chloro-phenyl)-3-[4-(3,4-dimethoxy-phenyl)-piperazin-1-yl]-3-oxo-propyl ester | 44.8% | 11.0% |
| Example 7: carbamic acid 3-[4-(3,4-dimethoxy-phenyl)-piperazin-1-yl]-1-(4-fluoro-phenyl)-3-oxo-propyl ester | 40.9% | 14.7% |
| Example 8: carbamic acid 3-[4-(3,4-dimethoxy-phenyl)-piperazin-1-yl]-3-oxo-1-p-tolyl-propyl ester | 30.1% | 10.9% |
| Example 9: carbamic acid 3-[4-(2,4-dimethoxy-phenyl)-piperazin-1-yl]-3-oxo-1-phenyl-propyl ester | 33.1% | 16.4% |
| Example 10: carbamic acid 3-[4-(3,5-dichloro-phenyl)-piperazin-1-yl]-3-oxo-1-phenyl-propyl ester | 26.0% | 14.8% |
| Example 11: carbamic acid 3-[4-(3,5-dimethoxy-phenyl)-piperazin-1-yl]-3-oxo-1-phenyl-propyl ester | 5.5% | 46.1% |
| Example 12: carbamic acid 3-[4-(2,3-dichloro-phenyl)-piperazin-1-yl]-3-oxo-1-phenyl-propyl ester | 37.0% | 46.8% |
| Example 13: carbamic acid 3-[4-(2,4-difluoro-phenyl)-piperazin-1-yl]-3-oxo-1-phenyl-propyl ester | 64.0% | 21.4% |
| Example 14: carbamic acid 3-(4-benzo[1,3]dioxol-5-yl-piperazin-1-yl)-3-oxo-1-phenyl-propyl ester | 64.0% | 17.8% |
| Example 15: carbamic acid 1-(4-methoxy-phenyl)-3-oxo-3-(4-phenyl-piperazin-1-yl)-propyl ester | 35.1% | 17.9% |
| Example 16: carbamic acid 1-(4-chloro-phenyl)-3-oxo-3-(4-phenyl-piperazin-1-yl)-propyl ester | 37.3% | 19.5% |
| Example 17: carbamic acid 3-[4-(4-tert-butyl-phenyl)-piperazin-1-yl]-3-oxo-1-phenyl-propyl ester | 25.3% | 29.4% |
| Example 18: carbamic acid 3-[4-(4-hydroxy-phenyl)-piperazin-1-yl]-3-oxo-1-phenyl-propyl ester | 30.6% | 26.4% |
| Example 19: dimethyl-carbamic acid 3-[4-(4-methoxy-phenyl)-piperazin-1-yl]-3-oxo-1-phenyl-propyl ester | 34.2% | 49.4% |
| Example 20: carbamic acid 3-[4-(3,4-dimethyl-phenyl)-piperazin-1-yl]-3-oxo-1-phenyl-propyl ester | 14.6% | 45.4% |
| Example 21: carbamic acid 3-{4-[bis-(4-fluoro-phenyl)-methyl]-piperazin-1-yl}-3-oxo-1-phenyl-propyl ester | 32.5% | 51.4% |
| Example 22: carbamic acid 3-oxo-1-phenyl-3-(4-quinoxalin-2-yl-piperazin-1-yl)-propyl ester | 29.4% | 38.0% |
| Example 23: acetic acid 4-[4-(3-carbamoyloxy-3-phenyl-propionyl)-piperazin-1-yl]-phenyl ester | 21.1% | 29.4% |

TABLE 1-continued

Results on acetic acid - induced writhing test and hot plate test) in mouse

| Compound | Writhing Test Suppression of pain response (10 mg/kg, p.o) | Hot Plate Test Increase in latency of avoidance response (30 mg/kg, p.o) |
|---|---|---|
| Example 24: carbamic acid 3-oxo-1-phenyl-3-(4-pyridin-2-yl-piperazin-1-yl)-propyl ester | 61.2% | 28.1% |
| Example 25: carbamic acid 3-oxo-1-phenyl-3-(4-pyrimidin-2-yl-piperazin-1-yl)-propyl ester | 59.3% | 15.9% |
| Example 26: carbamic acid 3-[4-(3,5-dichloro-pyridin-2-yl)-piperazin-1-yl]-3-oxo-1-phenyl-propyl ester | 30.8% | 20.6% |
| Example 27: carbamic acid 3-[4-(3-chloro-4-trifluoromethyl-phenyl)-piperazin-1-yl]-3-oxo-1-phenyl-propyl ester | 29.1% | 41.2% |
| Example 28: carbamic acid 3-oxo-1-phenyl-3-[4-(4-trifluoromethyl-phenyl)-piperazin-1-yl]-propyl ester | 55.6% | 3.1% |
| Example 29: carbamic acid 3-[4-(2-fluoro-phenyl)-piperazin-1-yl]-3-oxo-1-phenyl-propyl ester | 34.5% | 0.0% |
| Example 30: carbamic acid 3-[4-(3-fluoro-phenyl)-piperazin-1-yl]-3-oxo-1-phenyl-propyl ester | 9.2% | 27.1% |
| Example 31: carbamic acid 3-oxo-3-(4-phenyl-piperazin-1-yl)-1-(4-trifluoromethyl-phenyl)-propyl ester | 21.6% | 20.1% |
| Example 32: carbamic acid 3-oxo-3-(4-phenyl-piperazin-1-yl)-1-p-tolyl-propyl ester | 6.0% | 28.2% |
| Example 33: carbamic acid 3-[4-(3,4-difluoro-phenyl)-piperazin-1-yl]-3-oxo-1-phenyl-propyl ester | 74.5% | 43.6% |
| Example 34: carbamic acid 1-(4-nitro-phenyl)-3-oxo-3-(4-phenyl-piperazin-1-yl)-propyl ester | 38.4% | 0.6% |
| Example 35: carbamic acid 3-[4-(3,4-dimethoxy-phenyl)-piperazin-1-yl]-3-oxo-1-(4-trifluoromethyl-phenyl)-propyl ester; hydrochloride | 33.8% | 32.8% |
| Example 36: carbamic acid 3-[4-(3,4-dimethoxy-phenyl)-piperazin-1-yl]-1-(4-nitro-phenyl)-3-oxo-propyl ester; hydrochloride | 42.0% | 20.5% |
| Example 37: carbamic acid 3-[4-(3,4-dichloro-benzyl)-piperazin-1-yl]-3-oxo-1-phenyl-propyl ester | 38.1% | 10.0% |
| Example 38: carbamic acid 3-[4-(4-chloro-phenyl)-piperazin-1-yl]-3-oxo-1-phenyl-propyl ester | 66.1% | 38.3% |
| Example 39: carbamic acid 3-{4-[2-(3,4-dichloro-phenyl)-ethyl]-piperazin-1-yl}-3-oxo-1-phenyl-propyl ester | 23.2% | 18.7% |
| Example 40: carbamic acid 4-[4-(3,4-dichloro-phenyl)-piperazin-1-yl]-4-oxo-1-phenyl-butyl ester | 11.1% | 27.8% |
| Example 41: carbamic acid 4-[4-(3,4-dimethoxy-phenyl)-piperazin-1-yl]-4-oxo-1-phenyl-butyl ester | 31.2% | 28.7% |
| Example 43: carbamic acid 1-(2-chloro-phenyl)-3-oxo-3-(4-phenyl-piperazin-1-yl)-propyl ester | 46.0% | 26.7% |
| Example 45: carbamic acid 1-(3-trifluoro-phenyl)-3-oxo-3-(4-phenyl-piperazin-1-yl)-propyl ester | 19.0% | 6.9% |
| Example 46: carbamic acid 1-(3-bromo-phenyl)-3-oxo-3-(4-phenyl-piperazin-1-yl)-propyl ester | 71.3% | 33.1% |
| Example 47: carbamic acid 2,2-difluoro-3-oxo-1-phenyl-3-(4-phenyl-piperazin-1-yl)-propyl ester | 28.8% | 27.2% |

TABLE 1-continued

Results on acetic acid - induced writhing test and hot plate test) in mouse

| Compound | Writhing Test Suppression of pain response (10 mg/kg, p.o) | Hot Plate Test Increase in latency of avoidance response (30 mg/kg, p.o) |
|---|---|---|
| Example 49: carbamic acid-1-furan-3-yl-3-oxo-3-(4-phenyl-piperazin-1-yl)-propyl ester | 34.4% | 20.6% |
| Example 50: carbamic acid 1-(3-methyl-phenyl)-3-oxo-3-(4-phenyl-piperazin-1-yl)-propyl ester | 15.0% | 31.3% |
| Example 51: carbamic acid 1-(3-chloro-phenyl)-3-oxo-3-(4-phenyl-piperazin-1-yl)-propyl ester | 50.8% | 29.2% |
| Example 52: carbamic acid-2-(4-phenyl-piperazine-1-carbonyl)-1,2,3,4-tetrahydro-naphthalene-1-yl ester | 26.8% | 20.5% |
| Example 53: carbamic acid 1-(3,4-dichloro-phenyl)-3-oxo-3-(4-phenyl-piperazin-1-yl)-propyl ester | 28.5% | 10.6% |
| Example 55: carbamic acid 1-(3,5-trifluoromethyl-phenyl)-3-oxo-3-(4-phenyl-piperazin-1-yl)-propyl ester | 32.8% | 13.9% |
| Example 56: carbamic acid 1-(2,4-dichloro-phenyl)-3-oxo-3-(4-phenyl-piperazin-1-yl)-propyl ester | 23.3% | 11.8% |
| Example 57: carbamic acid 1-(2,5-difluoro-phenyl)-3-oxo-3-(4-phenyl-piperazin-1-yl)-propyl ester | 34.5% | 11.2% |
| Example 60: carbamic acid 1-(3,4-difluoro-phenyl)-3-oxo-3-(4-phenyl-piperazin-1-yl)-propyl ester | 28.0% | 17.2% |
| Example 61: (R)-carbamic acid 3-[4-(4-chloro-phenyl)-piperazin-1-yl]-3-oxo-1-phenyl-propyl ester | 24.1% | 38.8% |
| Example 62: (R)-carbamic acid 3-[4-(4-fluoro-phenyl)-piperazin-1-yl]-3-oxo-1-phenyl-propyl ester | 66.7% | 13.8% |
| Example 63: (R)-carbamic acid 3-[4-(4-ethoxy-phenyl)-piperazin-1-yl]-3-oxo-1-phenyl-propyl ester | 59.8% | 15.2% |
| Example 64: (S)-carbamic acid 3-[4-(3,4-difluoro-phenyl)-piperazin-1-yl]-3-oxo-1-phenyl-propyl ester | 41.1% | 33.0% |
| Example 65: (S)-carbamic acid 3-[4-(3,4-dimethoxy-phenyl)-piperazin-1-yl]-3-oxo-1-phenyl-propyl ester | 32.4% (30 mg/kg, p.o.) | 38.6% |
| Example 66: (S)-carbamic acid 3-[4-(3,4-dichloro-phenyl)-piperazin-1-yl]-3-oxo-1-phenyl-propyl ester | 62.5% | 27.8% |
| Example 67: (R)-carbamic acid 3-[4-(3,4-difluoro-phenyl)-piperazin-1-yl]-3-oxo-1-phenyl-propyl ester | 45.1% | 34.3% |
| Example 68: (R)-carbamic acid 3-[4-(3,4-dichloro-phenyl)-piperazin-1-yl]-3-oxo-1-phenyl-propyl ester | 51.0% | 15.7% |
| Example 69: (S)-carbamic acid 3-[4-(4-methoxy-phenyl)-piperazin-1-yl]-3-oxo-1-phenyl-propyl ester | 11.4% (30 mg/kg, p.o.) | 22.9% |
| Example 70: (R)-carbamic acid 3-[4-(4-methoxy-phenyl)-piperazin-1-yl]-3-oxo-1-phenyl-propyl ester | 59.8% | 30.6% |
| Example 71: (R)-carbamic acid 3-[4-(3,4-dimethoxy-phenyl)-piperazin-1-yl]-3-oxo-1-phenyl-propyl ester | 46.5% | 55.8% |
| Example 77: 4-[2-oxo-2-(4-phenyl-piperazin-1-yl)-ethyl]-1,4-dihydro-benzo[d][1,3]oxazin-2-one | 26.4% | 30.4% |
| Example 79: (S)-carbamic acid 3-[4-(4-fluoro)-phenyl piperazin-1-yl]-3-oxo-1-phenyl-propyl ester | 40.7% | 29.3% |
| Example 80: (R)-carbamic acid 3-[4-(4-methyl)-phenyl piperazin-1-yl]-3-oxo-1-phenyl-propyl ester | 36.3% | 16.7% |

TABLE 1-continued

Results on acetic acid - induced writhing test and hot plate test) in mouse

| Compound | Writhing Test Suppression of pain response (10 mg/kg, p.o) | Hot Plate Test Increase in latency of avoidance response (30 mg/kg, p.o) |
| --- | --- | --- |
| Example 81: (S)-carbamic acid 3-[4-(4-methyl)-phenyl piperazin-1-yl]-3-oxo-1-phenyl-propyl ester | 20.1% | 9.2% |
| Example 82: (R)-carbamic acid 3-[4-(2,4-difluoro)-phenyl piperazin-1-yl]-3-oxo-1-phenyl-propyl ester | 34.5% | 65.7% |
| Example 83: (R)-carbamic acid 3-[4-(4-hydroxy)-phenyl piperazin-1-yl]-3-oxo-1-phenyl-propyl ester | 44.5% | 89.3% |
| Example 84: (S)-carbamic acid 3-[4-(4-hydroxy)-phenyl piperazin-1-yl]-3-oxo-1-phenyl-propyl ester | 32.0% | 13.5% |
| Example 85: (S)-carbamic acid 3-[4-(4-chloro)-phenyl piperazin-1-yl]-3-oxo-1-phenyl-propyl ester | 52.0% | 25.3% |

Also, the compounds as listed above were tested for medicinal effects on the anxiety and depression through the following animal experiments.

4. Elevated Plus Maze (EPM) Test in Mouse

Elevated plus maze (EPM) is one of representative models that examine an anti-anxiety activity of a test material. Equipment used for an EPM test has a crossroad shape raised in a high position off the ground, and is configured in such a cliff shape that both sides of one road are protected with high walls and the other road is free from the wall. Among them, the road in the cliff shape is referred to as an 'open arm', and the road protected by the walls is referred to as a 'close arm'. In this case, a level of the anxiety of a mouse may be measured by determining in which arm the mouse stays longer. In general, the mouse stays longer in the close arm than the open arm, but a mouse treated with a medicine showing an anti-anxiety effect stays relatively longer in the open arm. A test material dissolved in a suitable vehicle was orally administered to a male ICR mouse weighing 20 to 25 g at an amount of 10 mg/kg. After 1 hour of the oral administration, the mouse was put on the center of an EPM equipment to measure how long the mouse stays in the open arm within a time range of 5 minutes. The anti-anxiety effect of the test material is represented by the 'Change index in Open-Arm Time' {[(open arm duration in test material-administered group–open arm duration in vehicle-administered group)/(open arm duration in vehicle administered group)]×100%}. From these results, it was observed that the increase of the open-arm time shows the increase in the anti-anxiety effect.

5. Test on Head Twitch Potentiation Induced by 5-HTP (5-HTP Potentiation Test) in Mouse When 5-hydroxy-L-tryptophan (5-HTP) is administered into a mouse, a head twitch phenomenon is observed since serotonin is increasingly secreted in the mouse. In this case, when the mouse is treated with a monoamineoxidase-A (MAO-A) suppressor that further potentiates serotonin activity, or an antidepressant agent such as a selective serotonin reuptake inhibitor (SSRI), the head twitch count of a mouse is significantly increased. By using this principle, it is possible to search an effect of the representative antidepressant agent. A test material dissolved in a suitable vehicle was orally administered to a male ICR mouse weighing 20 to 25 g at an amount of 30 mg/kg. After 30 minutes of the oral administration, 5-HTP (80 mg/kg) and 5-HTP peripheral decarbozylase inhibitor 'Carbidopa (25 mg/kg) were intraperitoneally administered to the mouse. After 30 minutes of the intraperitoneal administration, the mouse was put into an observation cage, and head twitches of the mouse were counted for 2 minutes. The anti-depression effect of the test material is represented by the 'Increase rate in Head Twitch No.' {[(Head Twitch No. of Test material-administered group–Head Twitch No. of vehicle-administered group)/(Head Twitch No. of vehicle-administered group)]×100%}. From these results, it was observed that the higher anti-depression effect is related to the 'higher increase of Head Twitch numbers.' Also, when the 'increase rate in Head Twitch numbers' is measured to be negative, it indicates that the corresponding compound serves as an antagonist to a 5-HT2A receptor (Darmani N A, *J. Neural Transm.*, 1998; 105 (6-7):635-643). In addition to the selective serotonin reuptake inhibitor (SSRI) that has been widely used as an antidepressant agent in the clinical fields, it was tested that 5-HT2A antagonists such as nefazodone and trazodone also have an antidepressant effect.

TABLE 2

Results on EPM (Elevated Plus Maze) test and 5-HTP - induced head twitch response test in mouse

| compound | Elevated Plus Maze Change index in Open-Arm Time (10 mg/kg, p.o) | 5-HTP Potentiation Increase rate in Head Twitch No. (30 mg/kg, p.o) |
| --- | --- | --- |
| Example 1: carbamic acid 3-[4-(4-fluoro-phenyl)-piperazin-1-yl]-3-oxo-1-phenyl-propyl ester | 25.6% | −65.7% |

TABLE 2-continued

Results on EPM (Elevated Plus Maze) test and 5-HTP - induced head twitch response test in mouse

| compound | Elevated Plus Maze Change index in Open-Arm Time (10 mg/kg, p.o) | 5-HTP Potentiation Increase rate in Head Twitch No. (30 mg/kg, p.o) |
|---|---|---|
| Example 3: carbamic acid 3-[4-(3,4-dichloro-phenyl)-piperazin-1-yl]-3-oxo-1-phenyl-propyl ester | 9.7% | 54.5% |
| Example 4: carbamic acid 3-oxo-1-phenyl-3-(4-p-tolyl-piperazin-1-yl)-propyl ester | 41.1% | −7.1% |
| Example 10: carbamic acid 3-[4-(3,5-dichloro-phenyl)-piperazin-1-yl]-3-oxo-1-phenyl-propyl ester | 27.3% | 85.7% |
| Example 11: carbamic acid 3-[4-(3,5-dimethoxy-phenyl)-piperazin-1-yl]-3-oxo-1-phenyl-propyl ester | 19.8% | 31.3% |
| Example 12: carbamic acid 3-[4-(2,3-dichloro-phenyl)-piperazin-1-yl]-3-oxo-1-phenyl-propyl ester | 41.1% | 10.0% |
| Example 13: carbamic acid 3-[4-(2,4-difluoro-phenyl)-piperazin-1-yl]-3-oxo-1-phenyl-propyl ester | 12.6% | −60.0% |
| Example 16: carbamic acid 1-(4-chloro-phenyl)-3-oxo-3-(4-phenyl-piperazin-1-yl)-propyl ester | 1.3% | 140.0% |
| Example 17: carbamic acid 3-[4-(4-tert-butyl-phenyl)-piperazin-1-yl]-3-oxo-1-phenyl-propyl ester | 34.0% | 10.0% |
| Example 18: carbamic acid 3-[4-(4-hydroxy-phenyl)-piperazin-1-yl]-3-oxo-1-phenyl-propyl ester | 16.1% | −23.4% |
| Example 19: dimethyl-carbamic acid 3-[4-(4-methoxy-phenyl)-piperazin-1-yl]-3-oxo-1-phenyl-propyl ester | 0.0% | 60.0% |
| Example 20: carbamic acid 3-[4-(3,4-dimethyl-phenyl)-piperazin-1-yl]-3-oxo-1-phenyl-propyl ester | 45.4% | −6.3% |
| Example 21: carbamic acid 3-{4-[bis-(4-fluoro-phenyl)-methyl]-piperazin-1-yl}-3-oxo-1-phenyl-propyl ester | 67.5% | −7.0% |
| Example 22: carbamic acid 3-oxo-1-phenyl-3-(4-quinoxalin-2-yl-piperazin-1-yl)-propyl ester | −21.2% | 3.9% |
| Example 23: acetic acid 4-[4-(3-carbamoyloxy-3-phenyl-propionyl)-piperazin-1-yl]-phenyl ester | −25.1% | 100.0% |
| Example 27: carbamic acid 3-[4-(3-chloro-4-trifluoromethyl-phenyl)-piperazin-1-yl]-3-oxo-1-phenyl-propyl ester | 66.7% | −78.1% |
| Example 28: carbamic acid 3-oxo-1-phenyl-3-[4-(4-trifluoromethyl-phenyl)-piperazin-1-yl]-propyl ester | −1.4% | −12.5% |
| Example 29: carbamic acid 3-[4-(2-fluoro-phenyl)-piperazin-1-yl]-3-oxo-1-phenyl-propyl ester | 92.3% | 14.3% |
| Example 30: carbamic acid 3-[4-(3-fluoro-phenyl)-piperazin-1-yl]-3-oxo-1-phenyl-propyl ester | 102.0% | 40.0% |
| Example 31: carbamic acid 3-oxo-3-(4-phenyl-piperazin-1-yl)-1-(4-trifluoromethyl-phenyl)-propyl ester | 35.6% | 10.0% |
| Example 32: carbamic acid 3-oxo-3-(4-phenyl-piperazin-1-yl)-1-p-tolyl-propyl ester | 9.5% | −40.0% |
| Example 34: carbamic acid 1-(4-nitro-phenyl)-3-oxo-3-(4-phenyl-piperazin-1-yl)-propyl ester | 6.5% | 2.9% |
| Example 35: carbamic acid 3-[4-(3,4-dimethoxy-phenyl)-piperazin-1-yl]-3-oxo-1-(4-trifluoromethyl-phenyl)-propyl ester; hydrochloride | 44.0% | 64.3% |

TABLE 2-continued

Results on EPM (Elevated Plus Maze) test and 5-HTP - induced head twitch response test in mouse

| compound | Elevated Plus Maze Change index in Open-Arm Time (10 mg/kg, p.o) | 5-HTP Potentiation Increase rate in Head Twitch No. (30 mg/kg, p.o) |
|---|---|---|
| Example 36: carbamic acid 3-[4-(3,4-dimethoxy-phenyl)-piperazin-1-yl]-1-(4-nitro-phenyl)-3-oxo-propyl ester; hydrochloride | 35.3% | 93.8% |
| Example 37: carbamic acid 3-[4-(3,4-dichloro-benzyl)-piperazin-1-yl]-3-oxo-1-phenyl-propyl ester | 98.8% | 166.7% |
| Example 39: carbamic acid 3-{4-[2-(3,4-dichloro-phenyl)-ethyl]-piperazin-1-yl}-3-oxo-1-phenyl-propyl ester | 57.8% | 319.0% |
| Example 40: carbamic acid 4-[4-(3,4-dichloro-phenyl)-piperazin-1-yl]-4-oxo-1-phenyl-butyl ester | 68.8% | 311.1% |
| Example 42: carbamic acid 1-(2-nitro-phenyl)-3-oxo-3-(4-phenyl-piperazin-1-yl)-propyl ester | 27.3% | 33.3% |
| Example 43: carbamic acid 1-(2-chloro-phenyl)-3-oxo-3-(4-phenyl-piperazin-1-yl)-propyl ester | 19.7% | 211.1% |
| Example 45: carbamic acid 1-(3-trifluoro-phenyl)-3-oxo-3-(4-phenyl-piperazin-1-yl)-propyl ester | 74.5% | 166.7% |
| Example 46: carbamic acid 1-(3-bromo-phenyl)-3-oxo-3-(4-phenyl-piperazin-1-yl)-propyl ester | 5.7% | 40.3% |
| Example 47: carbamic acid 2,2-difluoro-3-oxo-1-phenyl-3-(4-phenyl-piperazin-1-yl)-propyl ester | 21.4% | 22.5% |
| Example 49: carbamic acid-1-furan-3-yl-3-oxo-3-(4-phenyl-piperazin-1-yl)-propyl ester | 48.9% | −20.0% |
| Example 50: carbamic acid 1-(3-methyl-phenyl)-3-oxo-3-(4-phenyl-piperazin-1-yl)-propyl ester | 65.4% | −21.3% |
| Example 51: carbamic acid 1-(3-chloro-phenyl)-3-oxo-3-(4-phenyl-piperazin-1-yl)-propyl ester | −0.7% | 40.3% |
| Example 52: carbamic acid-2-(4-phenyl-piperazine-1-carbonyl)-1,2,3,4-tetrahydro-naphthalene-1-yl ester | 14.6% | 40.0% |
| Example 53: carbamic acid 1-(3,4-dichloro-phenyl)-3-oxo-3-(4-phenyl-piperazin-1-yl)-propyl ester | −17.7% | 50.0% |
| Example 55: carbamic acid 1-(3,5-trifluoromethyl-phenyl)-3-oxo-3-(4-phenyl-piperazin-1l-yl)-propyl ester | 13.8% | 22.5% |
| Example 56: carbamic acid 1-(2,4-dichloro-phenyl)-3-oxo-3-(4-phenyl-piperazin-1-yl)-propyl ester | 23.9% | 40.0% |
| Example 57: carbamic acid 1-(2,5-difluoro-phenyl)-3-oxo-3-(4-phenyl-piperazin-1-yl)-propyl ester | 88.8% | 27.9% |
| Example 60: carbamic acid 1-(3,4-difluoro-phenyl)-3-oxo-3-(4-phenyl-piperazin-1-yl)-propyl ester | 21.3% | −23.5% |
| Example 61: (R)-carbamic acid 3-[4-(4-chloro-phenyl)-piperazin-1-yl]-3-oxo-1-phenyl-propyl ester | −27.4% | 27.3% |
| Example 62: (R)-carbamic acid 3-[4-(4-fluoro-phenyl)-piperazin-1-yl]-3-oxo-1-phenyl-propyl ester | 2.7% | 0.8% |
| Example 63: (R)-carbamic acid 3-[4-(4-ethoxy-phenyl)-piperazin-1-yl]-3-oxo-1-phenyl-propyl ester | 25.0% | 19.5% |
| Example 64: (S)-carbamic acid 3-[4-(3,4-difluoro-phenyl)-piperazin-1-yl]-3-oxo-1-phenyl-propyl ester | 125.2% | 133.8% |

TABLE 2-continued

Results on EPM (Elevated Plus Maze) test and 5-HTP - induced head twitch response test in mouse

| compound | Elevated Plus Maze Change index in Open-Arm Time (10 mg/kg, p.o) | 5-HTP Potentiation Increase rate in Head Twitch No. (30 mg/kg, p.o) |
|---|---|---|
| Example 65: (S)-carbamic acid 3-[4-(3,4-dimethoxy-phenyl)-piperazin-1-yl]-3-oxo-1-phenyl-propyl ester | 74.7% | 91.6% |
| Example 66: (S)-carbamic acid 3-[4-(3,4-dichloro-phenyl)-piperazin-1-yl]-3-oxo-1-phenyl-propyl ester | 50.6% | −39.5% |
| Example 67: (R)-carbamic acid 3-[4-(3,4-difluoro-phenyl)-piperazin-1-yl]-3-oxo-1-phenyl-propyl ester | 34.3% | 58.8% |
| Example 68: (R)-carbamic acid 3-[4-(3,4-dichloro-phenyl)-piperazin-1-yl]-3-oxo-1-phenyl-propyl ester | 1.5% | −28.6% |
| Example 69: (S)-carbamic acid 3-[4-(4-methoxy-phenyl)-piperazin-1-yl]-3-oxo-1-phenyl-propyl ester | 57.3% | −14.3% |
| Example 70: : (R)-carbamic acid 3-[4-methoxy-phenyl)-piperazin-1-yl]-3-oxo-1-phenyl-propyl ester | 109% | 87.9% |
| Example 71: (R)-carbamic acid 3-[4-(3,4-dimethoxy-phenyl)-piperazin-1-yl]-3-oxo-1-phenyl-propyl ester | 125.4% | 126.7% |
| Example 77: 4-[2-oxo-2-(4-phenyl-piperazin-1-yl)-ethyl]-1,4-dihydro-benzo[d][1,3]oxazin-2-one | 4.9% | 25.0% |
| Example 79: (S)-carbamic acid 3-[4-(4-fluoro)-phenyl piperazin-1-yl]-3-oxo-1-phenyl-propyl ester | −5.1% | −30.0% |
| Example 80: (R)-carbamic acid 3-[4-(4-methyl)-phenyl piperazin-1-yl]-3-oxo-1-phenyl-propyl ester | 41.2% | 12.5% |
| Example 81: (S)-carbamic acid 3-[4-(4-methyl)-phenyl piperazin-1-yl]-3-oxo-1-phenyl-propyl ester | 23.0% | −21.4% |
| Example 82: (R)-carbamic acid 3-[4-(2,4-difluoro)-phenyl piperazin-1-yl]-3-oxo-1-phenyl-propyl ester | 62.6% | −20.0% |
| Example 83: (R)-carbamic acid 3-[4-(4-hydroxy)-phenyl piperazin-1-yl]-3-oxo-1-phenyl-propyl ester | 52.7% | 40.9% |
| Example 84: (S)-carbamic acid 3-[4-(4-hydroxy)-phenyl piperazin-1-yl]-3-oxo-1-phenyl-propyl ester | 65.6% | −37.5% |
| Example 85: (S)-carbamic acid 3-[4-(4-chloro)-phenyl piperazin-1-yl]-3-oxo-1-phenyl-propyl ester | 37.0% | 222.2% |

For the use in treating various diseases such as a wide range of pains (including acute pain, chronic pain, neuropathic pain, post-surgery neuropathic pain, diabetic neuropathic pain, postherpetic neuralgia, inflammatory pain, joint pain, and migraine headache and the like), anxiety and depression, the compound of the present invention is administered to patient, alone or in combinations with pharmaceutically available carriers. An exact dose of the administered compound may be determined according to the conditions of patients, the severity of patient status and the activity of the compound. Under the specific circumstances, the optimum dose of the administered compound should essentially be determined in a clinical manner, but be present within the scope of the present invention.

For the use of the compound according to the present invention, the compound is preferably administered orally since the compound is easily absorbed orally, but the present invention is not particularly limited thereto. For the oral administration, the compound according to the present invention is preferably used in combinations with a pharmaceutical carrier. A dose ratio of the carrier to the inventive compound is limited to allow the compound to take an effect on patients, and may be widely varied, depending on whether the composition is filled into a capsule, or formulated into a tablet. In the case of the tablet, edible and pharmaceutical carriers or mixtures thereof may be used herein. Examples of the suitable carriers includes, but are not particularly limited to, lactose, dibasic calcium phosphate and/or corn starch, and mixtures thereof, etc. Other pharmaceutically available compounds may be further added, including a lubricant such as magnesium stearate.

The invention claimed is:

1. A compound of Formula 1:

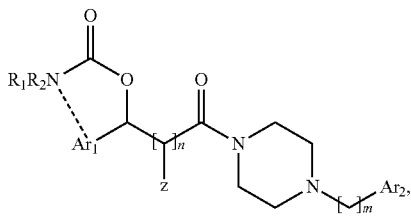

Formula 1 or a pharmaceutically acceptable salt or hydrate thereof, wherein - - - denotes an optional bond forming a cyclic moiety;

each of $R_1$ and $R_2$ is independently selected from the group consisting of H- and straight- or branched-chain $C_1$-$C_6$ alkyl, or $R_1$ and $R_2$ are taken together to form piperidinyl or piperazinyl, or $R_1$ and $R_2$ are taken together with $Ar_1$ to form benzo[d][1,3]oxazin-2-one moiety;

$Ar_1$ is selected from the group consisting of furanyl, methylenedioxyphenyl and phenyl which is optionally substituted by one or more substituents independently selected from the group consisting of H-, straight- or branched-chain $C_1$-$C_6$ alkyl, fluoro, chloro, bromo, straight- or branched-chain $C_1$-$C_6$ alkoxy, nitro and trifluoromethyl;

z is H- or fluoro;

$Ar_2$ is selected from the group consisting of phenyl, methylenedioxyphenyl, pyridinyl, pyrimidinyl, naphthyl, and quinoxalinyl, wherein $Ar_2$ is optionally substituted by one or more substituents independently selected from the group consisting of H-, straight- or branched-chain $C_1$-$C_6$ alkyl, hydroxy, halo, straight- or branched- chain $C_1$-$C_6$ alkoxy, nitro, acetyl, t-butylacetyl, trifluoromethyl, amino and acetyloxy;

n is 1 or 2; and m is 0, 1 or 2.

2. The compound of claim 1, which is a compound of Formula 2:

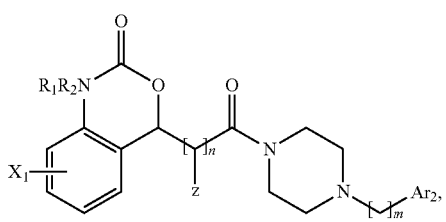

Formula 2 wherein each of $R_1$, $R_2$, z, n, m and $Ar_2$ is as defined in claim 1; and $X_1$ is one or more substituents independently selected from the group consisting of H-, straight- or branched-chain $C_1$-$C_6$ alkyl, fluoro, chloro, bromo, straight- or branched-chain $C_1$-$C_6$ alkoxy, nitro and trifluoromethyl.

3. The compound of claim 1, which is a compound of Formula 3:

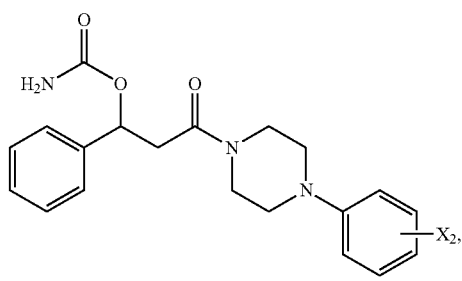

Formula 3 wherein $X_2$ is one or more substituents independently selected from the group consisting of H-, straight- or branched-chain $C_1$-$C_6$ alkyl, hydroxy, halo, straight- or branched-chain $C_1$-$C_6$ alkoxy, nitro, acetyl, t-butylacetyl, trifluoromethyl and amino.

4. The compound of claim 3, wherein $X_2$ is straight- or branched-chain $C_1$-$C_6$ alkoxy.

5. The compound of claim 3, wherein $X_2$ is two methoxy substituents.

6. The compound of claim 1, which is selected from the group consisting of:
carbamic acid 3-[4-(4-fluoro-phenyl)-piperazin-1-yl]-3-oxo-1-phenyl-propyl ester,
carbamic acid 3-[4-(4-methoxy-phenyl)-piperazin-1-yl]-3-oxo-1-phenyl-propyl ester,
carbamic acid 3-[4-(3,4-dichloro-phenyl)-piperazin-1-yl]-3-oxo-1-phenyl-propyl ester,
carbamic acid 3-oxo-1-phenyl-3-(4-p-tolyl-piperazin-1-yl)-propyl ester,
carbamic acid 3-[4-(3,4-dimethoxy-phenyl)-piperazin-1-yl]-3-oxo-1-phenyl-propyl ester,
carbamic acid 1-(4-chloro-phenyl)-3-[4-(3,4-dimethoxy-phenyl)-piperazin-1-yl]-3-oxo-propyl ester,
carbamic acid 3-[4-(3,4-dimethoxy-phenyl)-piperazin-1-yl]-1-(4-flouro-phenyl)-3-oxo-propyl ester,
carbamic acid 3-[4-(3,4-dimethoxy-phenyl)-piperazin-1-yl]-3-oxo-1-p-tolyl-propyl ester,
carbamic acid 3-[4-(2,4-dimethoxy-phenyl)-piperazin-1-yl]-3-oxo-1-phenyl-propyl ester,
carbamic acid 3-[4-(3,5-dichloro-phenyl)-piperazin-1-yl]-3-oxo-1-phenyl-propyl ester,
carbamic acid 3-[4-(3,5-dimethoxy-phenyl)-piperazin-1-yl]-3-oxo-1-phenyl-propyl ester,
carbamic acid 3-[4-(2,3-dichloro-phenyl)-piperazin-1-yl]-3-oxo-1-phenyl-propyl ester,
carbamic acid 3-[4-(2,4-difluoro-phenyl)-piperazin-1-yl]-3-oxo-1-phenyl-propyl ester,
carbamic acid 3-(4-benzo[1,3]dioxol-5-yl-piperazin-1-yl)-3-oxo-1-phenyl-propyl ester,
carbamic acid 1-(4-methoxy-phenyl)-3-oxo-3-(4-phenyl-piperazin-1-yl)-propyl ester,
carbamic acid 1-(4-chloro-phenyl)-3-oxo-3-(4-phenyl-piperazin-1-yl)-propyl ester,
carbamic acid 3-[4-(4-tert-butyl-phenyl)-piperazin-1-yl]-3-oxo-1-phenyl-propyl ester,
carbamic acid 3-[4-(4-hydroxy-phenyl)-piperazin-1-yl]-3-oxo-1-phenyl-propyl ester,
dimethyl-carbamic acid 3-[4-(4-methoxy-phenyl)-piperazin-1 -yl]-3-oxo-1 -phenyl- propyl ester, carbamic acid 3-[4-(3,4-dimethyl-phenyl)-piperazin-1-yl]-3-oxo-1-phenyl-propyl ester,
carbamic acid 3-oxo-1-phenyl-3-(4-quinoxalin-2-yl-piperazin-1-yl)-propyl ester,
acetic acid 4-[4-(3-carbamoyloxy-3-phenyl-propionyl)-piperazin-1-yl]-phenyl ester,
carbamic acid 3-oxo-1-phenyl-3-(4-pyridin-2-yl-piperazin-1-yl)-propyl ester,
carbamic acid 3-oxo-1-phenyl-3-(4-pyrimidin-2-yl-piperazin-1-yl)-propyl ester,
carbamic acid 3-[4-(3,5-dichloro-pyridin-2-yl)-piperazin-1-yl]-3-oxo-1-phenyl-propyl ester,
carbamic acid 3-[4-(4-chloro-3-trifluoromethyl-phenyl)-piperazin-1-yl]-3-oxo-1-phenyl-propyl ester,
carbamic acid 3-oxo-1-phenyl-3[4-(4-trifluoromethyl-phenyl)-piperazin-1-yl]-propyl ester,
carbamic acid 3-[4-(2-flouro-phenyl)-piperazin-1-yl]-3-oxo-1-phenyl-propyl ester,
carbamic acid 3-[4-(3-flouro-phenyl)-piperazin-1-yl]-3-oxo-1-phenyl-propyl ester,
carbamic acid 3-oxo-3-(4-phenyl-piperazin-1 -yl)-1 -(4-trifluoromethyl-phenyl)-propyl ester,
carbamic acid 3-oxo-3-(4-phenyl-piperazin-1-yl)-1-p-tolyl-propyl ester,
carbamic acid 3-[4-(3,4-difluoro-phenyl)-piperazin-1-yl]-3-oxo-1-phenyl-propyl ester,
carbamic acid 1 -(4-nitro-phenyl)-3-oxo-3-(4-phenylpiperazin-1 -yl)-propyl ester,
carbamic acid 3-[4-(3,4-dimethoxy-phenyl)-piperazin-1-yl]-3-oxo-1-(4-trifluoromethyl-phenyl)-propyl ester,
carbamic acid 3-[4-(3,4-dimethoxy-phenyl)-piperazin-1-yl]-1-(4-nitro-phenyl)-3-oxo-propyl ester,
carbamic acid 3-[4-(3,4-dichloro-benzyl)-piperazin-1-yl]-3-oxo-1-phenyl-propyl ester,
carbamic acid 3-[4-(4-chloro-phenyl)-piperazin-1-yl]-3-oxo-1-phenyl-propyl ester,
carbamic acid 3-{4-[2-(3,4-dichloro-phenyl)-ethyl]-1-piperazin-1 -yl}-3-oxo-1 -phenyl-propyl ester,
carbamic acid 4-[4-(3,4-dichloro-phenyl)-piperazin-1 -yl]-4-oxo-1 -phenyl-butyl ester,
carbamic acid 4-[4-(3,4-dimethoxy-phenyl)-piperazin-1 -yl]-4-oxo-1 -phenyl-butyl ester,
carbamic acid 1-(2-nitro-phenyl)-3-oxo-3-(4-phenylpiperazin-1-yl)-propyl ester,
carbamic acid 1-(2-chloro-phenyl)-3-oxo-3-(4-phenylpiperazin-1-yl)-propyl ester,
carbamic acid 1-(2-methoxy-phenyl)-3-oxo-3-(4-phenylpiperazin-1-yl)-propyl ester
carbamic acid 1-(3-trifluoromethyl-phenyl)-3-oxo-3-(4-phenylpiperazin-1-yl)-propyl ester,
carbamic acid 1-(3-bromo-phenyl)-3-oxo-3-(4-phenylpiperazin-1-yl)-propyl ester,
carbamic acid 1-(3,4-dimethoxy-phenyl)-3-oxo-3-(4-phenylpiperazin-1-yl)-propyl ester,
carbamic acid 1-furan-3-yl-3-oxo-3-(4-phenyl-piperazin-1-yl)-propyl ester,
carbamic acid 1-(3-methyl-phenyl)-3-oxo-3-(4-phenyl-piperazin-1-yl)-propyl ester,
carbamic acid 1-(3-chloro-phenyl)-3-oxo-3-(4-phenyl-piperazin-1-yl)-propyl ester,
carbamic acid 1-(3,4-dichloro-phenyl)-3-oxo-3-(4-phenyl-piperazin-1-yl)-propyl ester,
carbamic acid 1-(2,3,4,5,6-pentafluoro-phenyl)-3-oxo-3-(4-phenyl-piperazin-1-yl)-propyl ester,
carbamic acid 1-(3,5-di-trifluoromethyl-phenyl)-3-oxo-3-(4-phenyl-piperazin-1-yl)-propyl ester,
carbamic acid 1-(2,4-dichloro-phenyl)-3-oxo-3-(4-phenyl-piperazin-1-yl)-propyl ester,
carbamic acid 1-(2,5-difluoro-phenyl)-3-oxo-3-(4-phenyl-piperazin-1-yl)-propyl ester,
carbamic acid 1-(2,4-dimethyl-phenyl)-3-oxo-3-(4-phenyl-piperazin-1-yl)-propyl ester,
carbamic acid 1-(3,4-methylenedioxy-phenyl)-3-oxo-3-(4-phenyl-piperazin-1-yl)- propyl ester,
carbamic acid 1-(3,4-difluoro-phenyl)-3-oxo-3-(4-phenyl-piperazin-1-yl)-propyl ester, and
4-[2-oxo-2-(4-phenyl-piperazin-1-yl)-ethyl]-1,4-dihydro-benzo[d][1,3]oxazin-2-one.

7. The compound of claim 1, which is selected from the group consisting of:
carbamic acid 3-[4-(4-fluoro-phenyl)-piperazin-1-yl]-3-oxo-1-phenyl-propyl ester,
carbamic acid 3-[4-(3,4-dichloro-benzyl)-piperazin-1-yl]-3-oxo-1-phenyl-propyl ester,
carbamic acid 4-[4-(3,4-dichloro-phenyl)-piperazin-1-yl]-4-oxo-1-phenyl-butyl ester,
carbamic acid 3-[4-(3,4-dichloro-phenyl)-piperazin-1-yl]-3-oxo-1-phenyl-propyl ester,
carbamic acid 3-[4-(4-methyl-phenyl)-piperazin-1-yl]-3-oxo-1-phenyl-propyl ester,
carbamic acid 3-[4-(2,4-difluoro-phenyl)-piperazin-1-yl]-3-oxo-1-phenyl-propyl ester,
carbamic acid 3-[4-(3-chloro-4-trifluoromethyl-phenyl)-piperazin-1-yl]-3-oxo-1-phenyl-propyl ester, and
carbamic acid 3-oxo-1-phenyl-3-[4-(4-trifluoromethyl-phenyl)-piperazin-1-yl]-propyl ester.

8. The compound of claim 1, wherein the compound is carbamic acid 3-[4-(3,4- dimethoxy-phenyl)-piperazin-1-yl]-3-oxo-1-phenyl-propyl ester.

9. The compound of claim 1, which is selected from the group consisting of:
(R)-carbamic acid 3-[4-(4-chloro-phenyl)-piperazin-1-yl]-3-oxo-1-phenyl-propyl ester,
(R)-carbamic acid 3-[4-(4-flouro-phenyl)-piperazin-1-yl]-3-oxo-1-phenyl-propyl ester,
(R)-carbamic acid 3-[4-(4-ethoxy-phenyl)-piperazin-1-yl]-3-oxo-1-phenyl-propyl ester,
(S)-carbamic acid 3-[4-(3,4-difluoro-phenyl)-piperazin-1-yl]-3-oxo-1-phenyl-propyl ester,
(S)-carbamic acid 3-[4-(3,4-dimethoxy-phenyl)-piperazin-1-yl]-3-oxo-1-phenyl-propyl ester,
(S)-carbamic acid 3-[4-(3,4-dichloro-phenyl)-piperazin-1-yl]-3-oxo-1-phenyl-propyl ester,
(R)-carbamic acid 3-[4-(3,4-difluoro-phenyl)-piperazin-1-yl]-3-oxo-1-phenyl-propyl ester,
(R)-carbamic acid 3-[4-(3,4-dichloro-phenyl)-piperazin-1-yl]-3-oxo-1-phenyl-propyl ester,
(S)-carbamic acid 3-[4-(4-methoxy-phenyl)-piperazin-1-yl]-3-oxo-1-phenyl-propyl ester,
(R)-carbamic acid 3-[4-(4-methoxy-phenyl)-piperazin-1-yl]-3-oxo-1-phenyl-propyl ester,
(R)-carbamic acid 3-[4-(3,4-dimethoxy-phenyl)-piperazin-1-yl]-3-oxo-1-phenyl-propyl ester,
piperidine -1-carboxylic acid-(R)-3-[4-(3,4-dimethoxy-phenyl)-piperazin-1-yl]-3-oxo-1-phenyl propyl ester,
butyl-carbamic acid-(R)-3-[4-(3,4-dimethoxy-phenyl)-piperazin-1-yl]-3-oxo-1-phenyl-propyl ester,
(R)-carbamic acid 3-[4-(4-amino-phenyl)-piperazin-1-yl]-3-oxo-1-phenyl-propyl ester,
(R)-carbamic acid 3-[4-(3-hydroxy-4-methoxy-phenyl)-piperazin-1-yl]-3-oxo-1-phenyl-propyl ester,
(S)-carbamic acid 3-[4-(4-fluoro-phenyl)-piperazin-1-yl]-3-oxo-1-phenyl-propyl ester, (R)-carbamic acid 3-[4-(4-methyl-phenyl)-piperazin-1-yl]-3-oxo-1-phenyl-propyl ester, (S)-carbamic acid 3-[4-(4-methyl-phenyl)-piperazin-1-yl]-3-oxo-1-phenyl-propyl ester, (R)-carbamic acid 3-[4-(2,4-difluoro-phenyl)-piperazin-1-yl]-3-oxo-1-phenyl-propyl ester, (R)-carbamic acid 3-[4-(4-hydroxy-phenyl)-piperazin-1-yl]-3-oxo-1-phenyl-propyl ester, (S)-carbamic acid 3-[4-(4-hydroxy-phenyl)-piperazin-1-yl]-3-oxo-1-phenyl-propyl ester, (S)-carbamic acid 3-[4-(4-chloro-phenyl)-piperazin-1-yl]-3-oxo-1-phenyl-propyl ester, carbamic acid (R)-3-[4-(3-hydroxy-4-methoxy-phenyl)-piperazin-1-yl]-3-oxo-1-phenyl-propyl ester, and carbamic acid (R)-3-[4-(3-methoxy-4-hydroxy-phenyl)-piperazin-1-yl]-3-oxo-1-phenyl-propyl ester.

10. The compound of claim 1, which is selected from the group consisting of:

(R)-carbamic acid 3-[4-(4-fluoro-phenyl)-piperazin-1-yl]-3-oxo-1-phenyl-propyl ester, (R)-carbamic acid 3-[4-(4-methoxy-phenyl)-piperazin-1-yl]-3-oxo-1-phenyl-propyl ester, (S)-carbamic acid 3-[4-(3,4-dichloro-phenyl)-piperazin-1-yl]-3-oxo-1-phenyl-propyl ester, (S)-carbamic acid 3-[4-(3,4-dimethoxy-phenyl)-piperazin-1-yl]-3-oxo-1-phenyl-propyl ester, (R)-carbamic acid 3-[4-(3,4-dimethoxy-phenyl)-piperazin-1-yl]-3-oxo-1-phenyl-propyl ester, (S)-carbamic acid 3-[4-(3,4-difluoro-phenyl)-piperazin-1-yl]-3-oxo-1-phenyl-propyl ester, (R)-carbamic acid 3-[4-(3,4-difluoro-phenyl)-piperazin-1-yl]-3-oxo-1-phenyl-propyl ester, (R)-carbamic acid 3-[4-(4-hydroxy-phenyl)-piperazin-1-yl]-3-oxo-1-phenyl-propyl ester, and (S)-carbamic acid 3-[4-(4-chloro-phenyl)-piperazin-1-yl]-3-oxo-1-phenyl-propyl ester.

11. The compound of claim 1, wherein the compound is (R)-carbamic acid 3-[4-(3,4-dimethoxy-phenyl)-piperazin-1-yl]-3-oxo-1-phenyl-propyl ester.

12. The compound of claim 1, wherein the pharmaceutically acceptable salt is selected from the group consisting of methanesulfonate and hydrochloride.

13. A compound which is selected from the group consisting of:

carbamic acid 3-{4-[bis-(4-flouro-phenyl)-methyl]-piperazin-1-yl}-3-oxo-1-phenyl-propyl ester, carbamic acid 2,2-difluoro-3-oxo-1-phenyl-3-(4-phenylpiperazin-1-yl)-propyl ester, carbamic acid 2-(4-phenyl-piperazine-1-carbonyl)-1,2,3,4-tetrahydro-naphthalen-1-yl ester, phenethyl-carbamic acid-(R)-3-[4-(3,4-dimethoxy-phenyl)-piperazin-1-yl]-3-oxo-1-phenyl-propyl ester, and 4-methyl-piperazine-1-carboxylic acid-(R)-3-[4-(3,4-dimethoxy-phenyl)-piperazin-1-yl]-3-oxo-1-phenyl-propyl ester.

14. A pharmaceutical composition comprising a therapeutically effective amount of the compound of claim 1 and a pharmaceutically acceptable carrier.

15. The pharmaceutical composition of claim 14, wherein the compound is selected from the group consisting of:

carbamic acid 3-[4-(4-fluoro-phenyl)-piperazin-1-yl]-3-oxo-1-phenyl-propyl ester, carbamic acid 3-[4-(3,4-dichloro-benzyl)-piperazin-1-yl]-3-oxo-1-phenyl-propyl ester, carbamic acid 4-[4-(3,4-dichloro-phenyl)-piperazin-1-yl]-4-oxo-1-phenyl-butyl ester, carbamic acid 3-[4-(3,4-dichloro-phenyl)-piperazin-1-yl]-3-oxo-1-phenyl-propyl ester, carbamic acid 3-[4-(4-methyl-phenyl)-piperazin-1-yl]-3-oxo-1-phenyl-propyl ester, carbamic acid 3-[4-(2,4-difluoro-phenyl)-piperazin-1-yl]-3-oxo-1-phenyl-propyl ester, carbamic acid 3-[4-(3-chloro-4-trifluoromethyl-phenyl)-piperazin-1-yl]-3-oxo-1-phenyl-propyl ester, and carbamic acid 3-oxo-1-phenyl-3-[4-(4-trifluoromethyl-phenyl)-piperazin-1-yl]-propyl ester.

16. The pharmaceutical composition of claim 14, wherein the compound is carbamic acid 3-[4-(3,4-dimethoxy-phenyl)-piperazin-1-yl]-3-oxo-1-phenyl-propyl ester.

17. The pharmaceutical composition of claim 14, wherein the compound is selected from the group consisting of:

(R)-carbamic acid 3-[4-(4-fluoro-phenyl)-piperazin-1-yl]-3-oxo-1-phenyl-propyl ester, (R)-carbamic acid 3-[4-(4-methoxy-phenyl)-piperazin-1-yl]-3-oxo-1-phenyl-propyl ester, (S)-carbamic acid 3-[4-(3,4-dichloro-phenyl)-piperazin-1-yl]-3-oxo-1-phenyl-propyl ester, (S)-carbamic acid 3-[4-(3,4-dimethoxy-phenyl)-piperazin-1-yl]-3-oxo-1-phenyl-propyl ester, (R)-carbamic acid 3-[4-(3,4-dimethoxy-phenyl)-piperazin-1-yl]-3-oxo-1-phenyl-propyl ester, (S)-carbamic acid 3-[4-(3,4-difluoro-phenyl)-piperazin-1-yl]-3-oxo-1-phenyl-propyl ester, (R)-carbamic acid 3-[4-(3,4-difluoro-phenyl)-piperazin-1-yl]-3-oxo-1-phenyl-propyl ester, (R)-carbamic acid 3-[4-(4-hydroxy-phenyl)-piperazin-1-yl]-3-oxo-1-phenyl-propyl ester, and (S)-carbamic acid 3-[4-(4-chloro-phenyl)-piperazin-1-yl]-3-oxo-1-phenyl-propyl ester.

18. The pharmaceutical composition of claim 14, wherein the compound is (R)-carbamic acid 3-[4-(3,4-dimethoxy-phenyl)-piperazin-1-yl]-3-oxo-1-phenyl-propyl ester.

19. The pharmaceutical composition of claim 14, wherein the therapeutically effect amount is in the range of 20 to 500 mg.

* * * * *